United States Patent
Butzke et al.

(10) Patent No.: US 7,074,889 B2
(45) Date of Patent: Jul. 11, 2006

(54) **IDENTIFICATION OF A NEW CYTOTOXIC ACTIVITY FROM THE INK OF *APLYSIA PUNCTATA***

(75) Inventors: Daniel Butzke, Berlin (DE); Nikolaus Machuy, Berlin (DE); Thomas Rudel, Berlin (DE); Thomas F. Meyer, Berlin (DE)

(73) Assignee: Max-Planck-Gesellschaft zur Foerderung der Wissenschaften. E.V., Munich (DE)

( * ) Notice: Subject to any disclaimer, the term of this patent is extended or adjusted under 35 U.S.C. 154(b) by 0 days.

(21) Appl. No.: 10/399,241

(22) PCT Filed: Oct. 12, 2001

(86) PCT No.: PCT/EP01/11837

§ 371 (c)(1),
(2), (4) Date: Sep. 23, 2003

(87) PCT Pub. No.: WO02/31144

PCT Pub. Date: Apr. 18, 2002

(65) Prior Publication Data

US 2004/0101940 A1    May 27, 2004

(30) Foreign Application Priority Data

Oct. 13, 2000    (EP) .................................. 00122466

(51) Int. Cl.
*A61K 38/00*    (2006.01)

(52) U.S. Cl. .......................... 530/300; 530/350; 514/2; 424/185.1

(58) Field of Classification Search ................ 530/300, 530/350

See application file for complete search history.

(56) References Cited

U.S. PATENT DOCUMENTS

| 4,414,205 A | * | 11/1983 | Pettit ........................... 514/21 |
| 6,171,818 B1 | * | 1/2001 | Petzelt ...................... 435/69.1 |
| 2004/0029129 A1 | * | 2/2004 | Wang et al. ................... 435/6 |

FOREIGN PATENT DOCUMENTS

| WO | WO 97/16457 A | 5/1997 |
| WO | WO 98/52971 A | 11/1998 |

OTHER PUBLICATIONS

Kamiya, H. et al. Toxicon. 1989; 27(12): 1269-1277 (Abstract).*
Yamazaki M. et al., "Antitumor and Antimicrobial Glycoproteins from Sea Hares" Comparative Biochemistry and Physiology, 1993, vol. 105C, No. 2, pp. 141-146, XP002034987.
Yamazaki M. et al., "Purification of a Cytolytic Factor From Purple Fluid of a Sea-Hare Aplysia-Kurodai" FEBS Letters, 1986, vol. 198, No. 1, pp. 25-28, XP001002735.
Takamatsu N. et al., "Molecular Cloning of the Defense Factor in the Albumen Gland of the Sea Hare Aplysia Kurodai" FEBS Letters, Elsevier Science Publishers, 1995, vol. 377, No. 3, pp. 373-376, XP002035003.

* cited by examiner

*Primary Examiner*—Jon Weber
*Assistant Examiner*—Anand Desai
(74) *Attorney, Agent, or Firm*—Rothwell, Figg, Ernst & Manbeck, P.C.

(57) ABSTRACT

The present invention relates to novel proteins having cytotoxic activity derived from the sea hare *Aplysia*.

10 Claims, 21 Drawing Sheets

Figure 2:
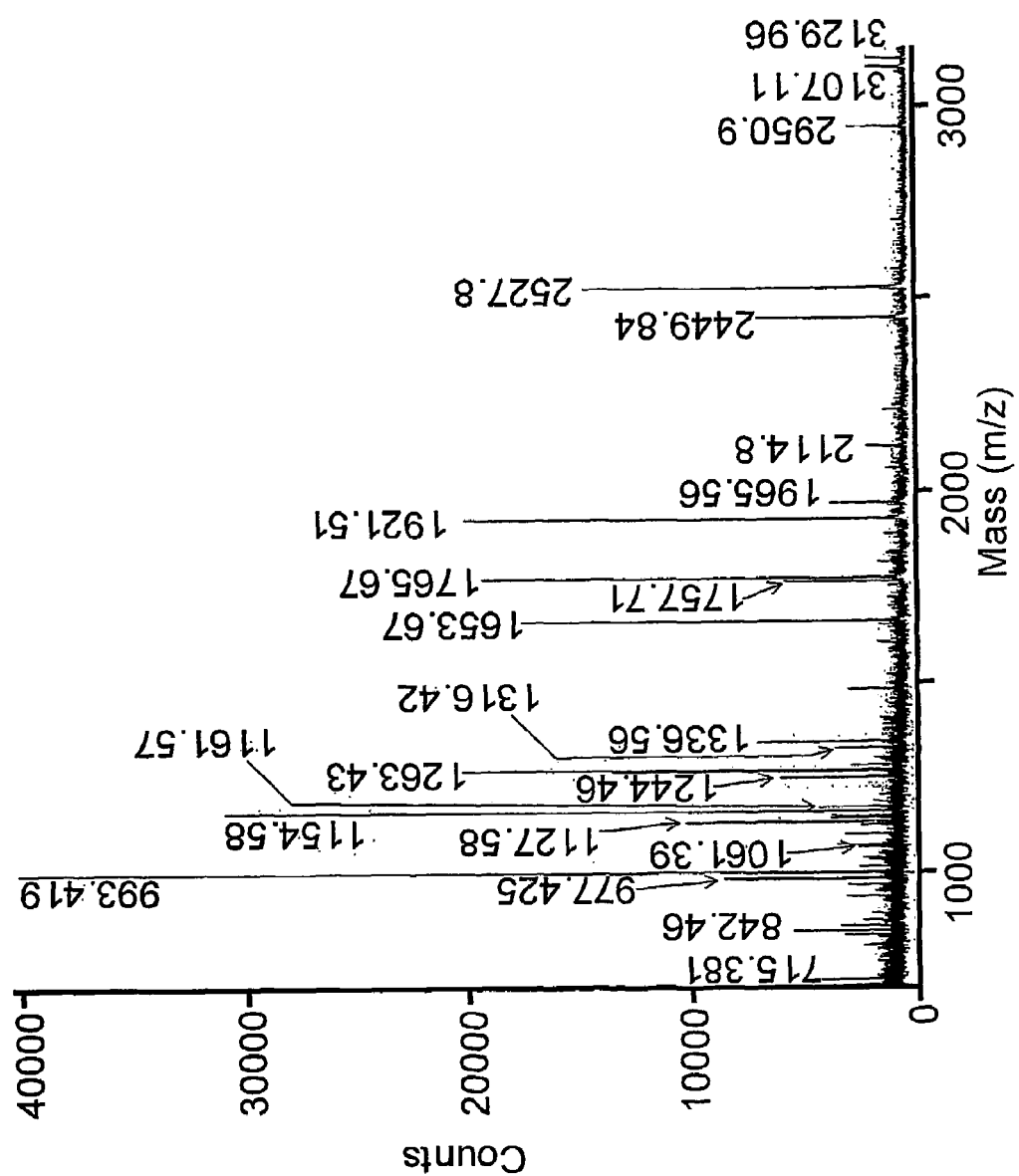

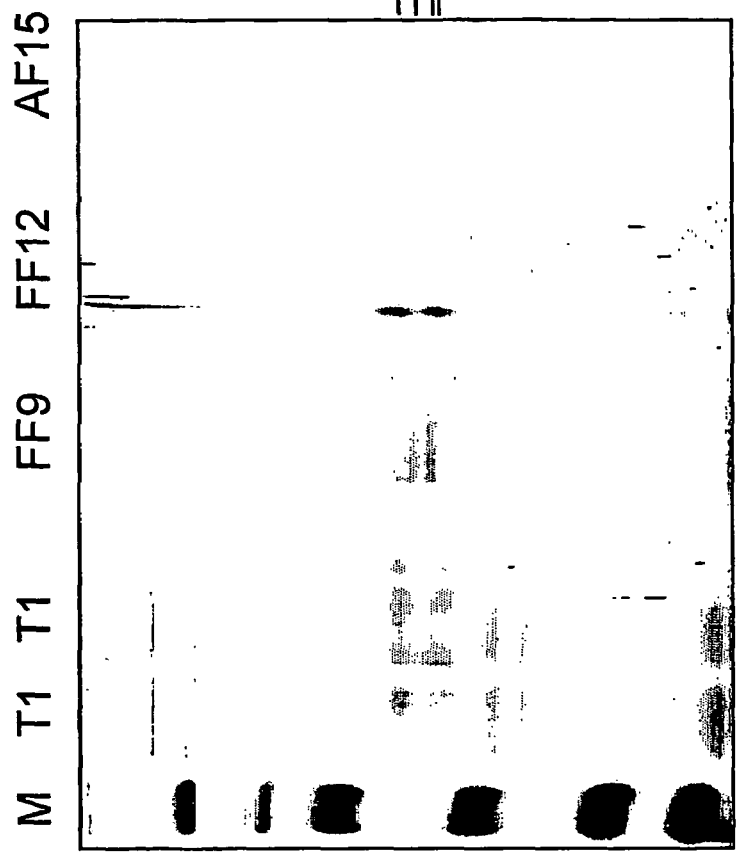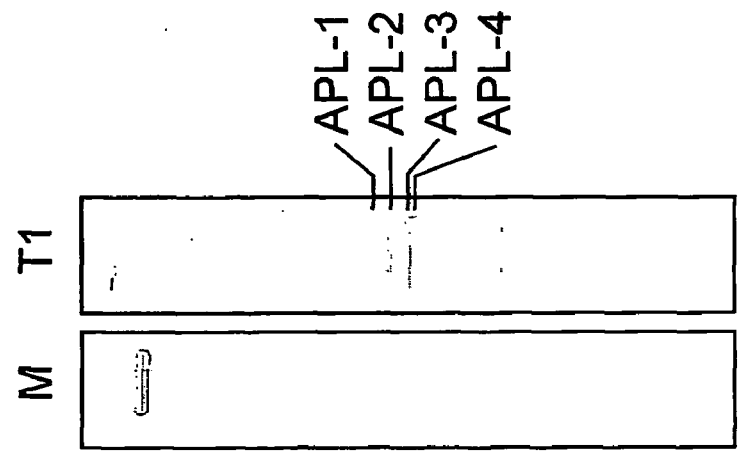
Fig.1

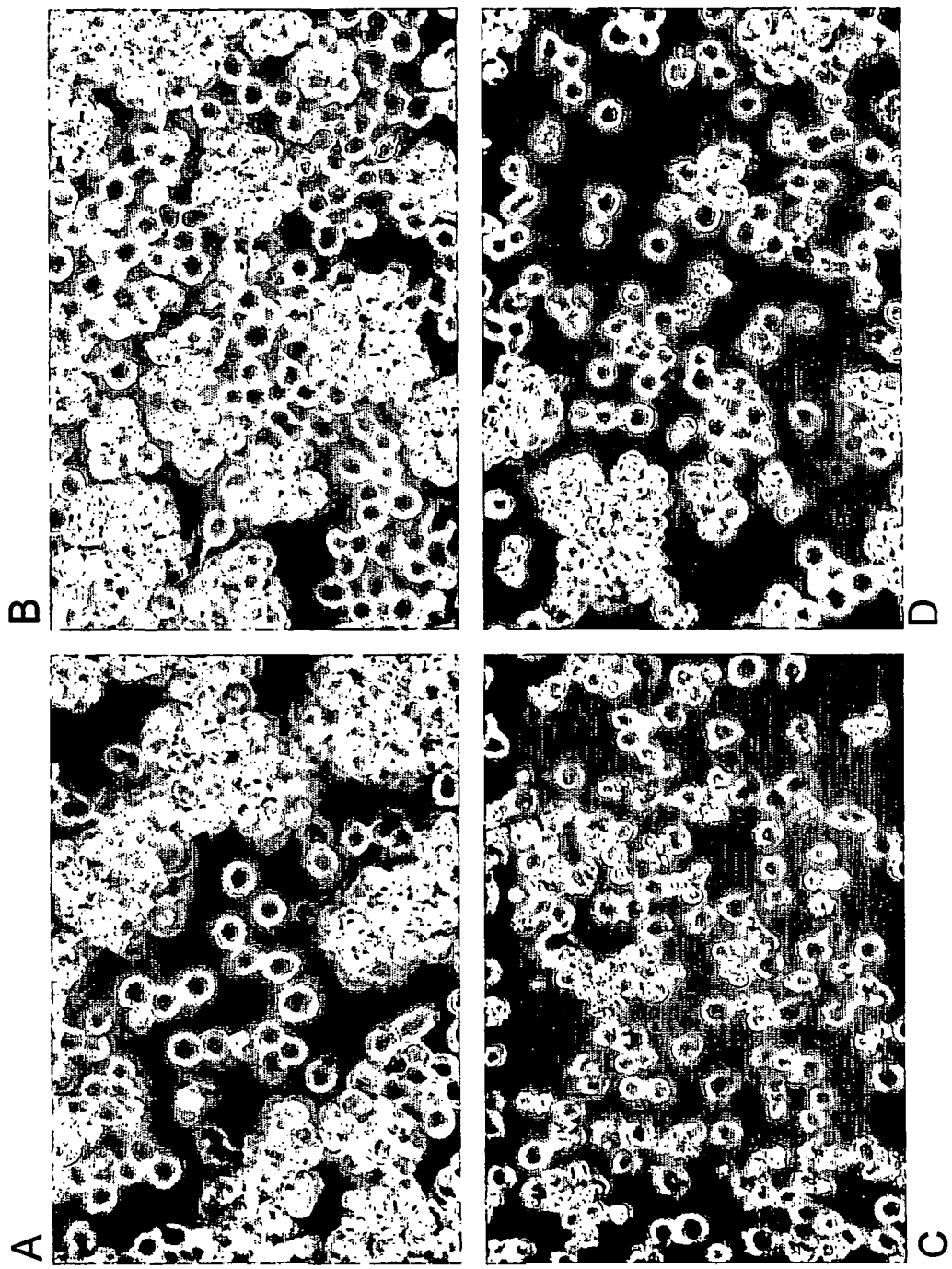
Fig. 8A-D

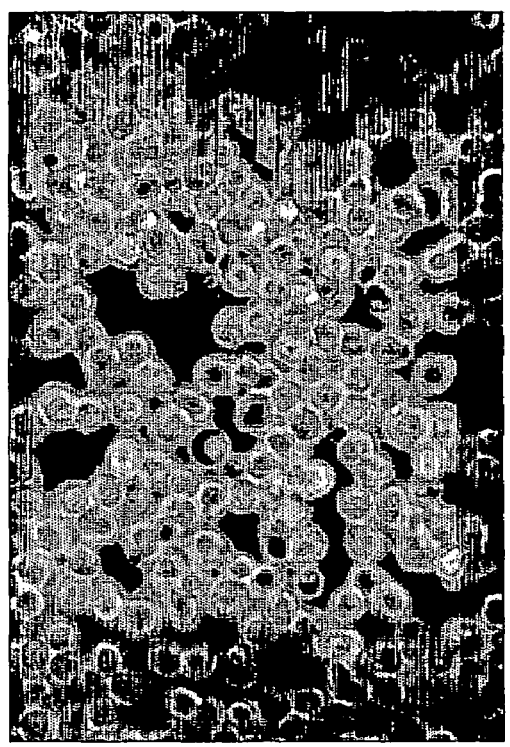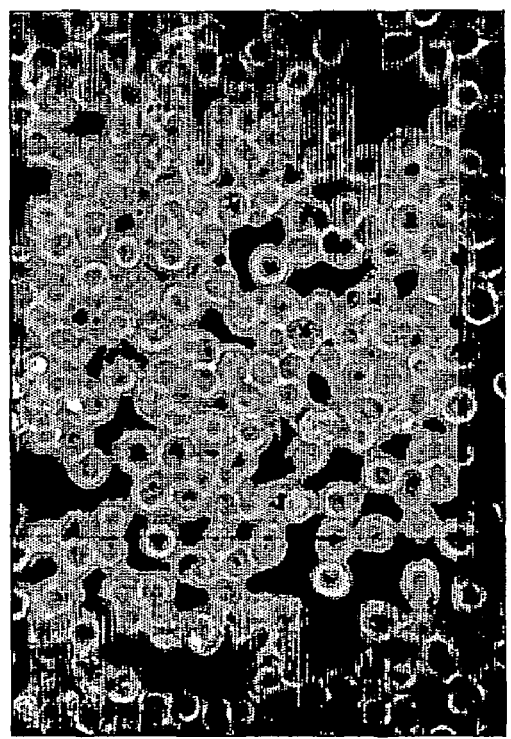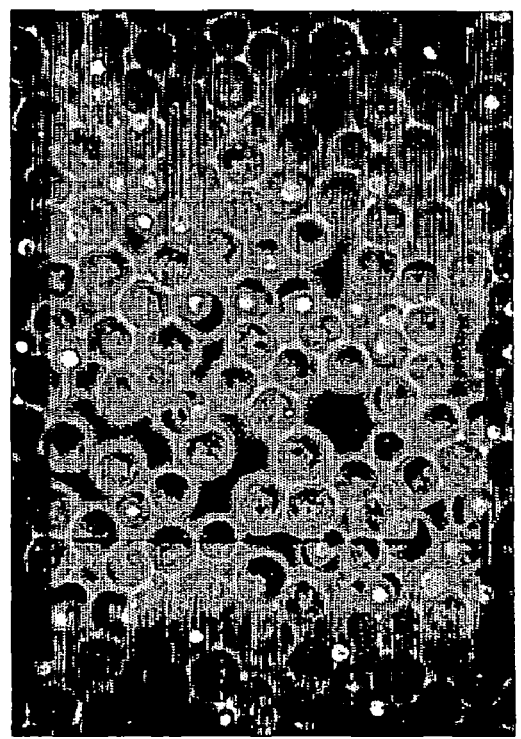
Fig. 8E-G

Fig. 18
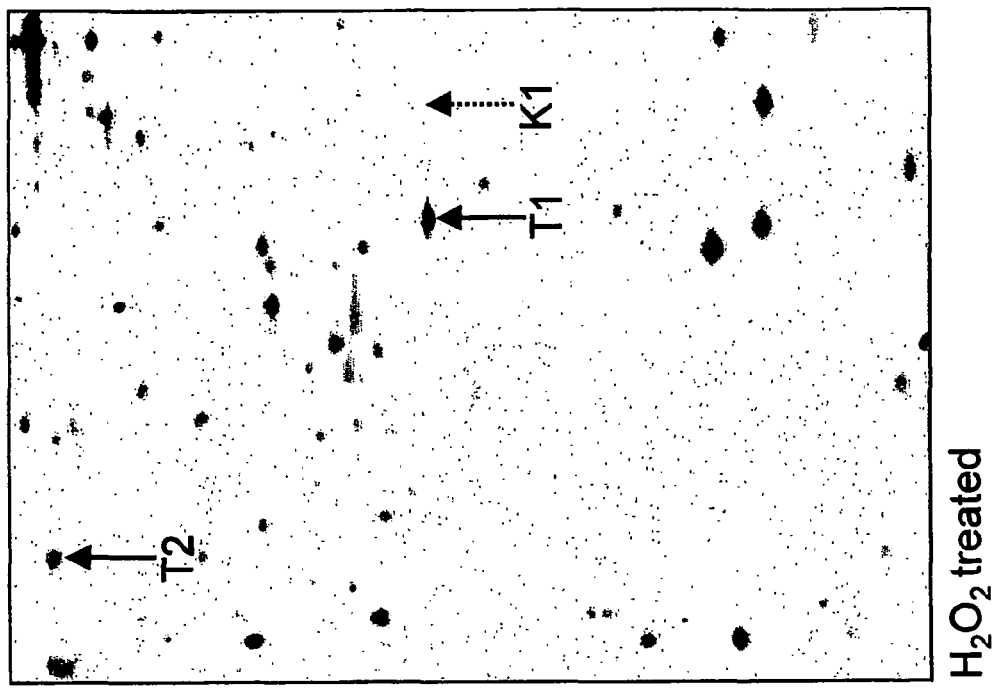
H₂O₂ treated
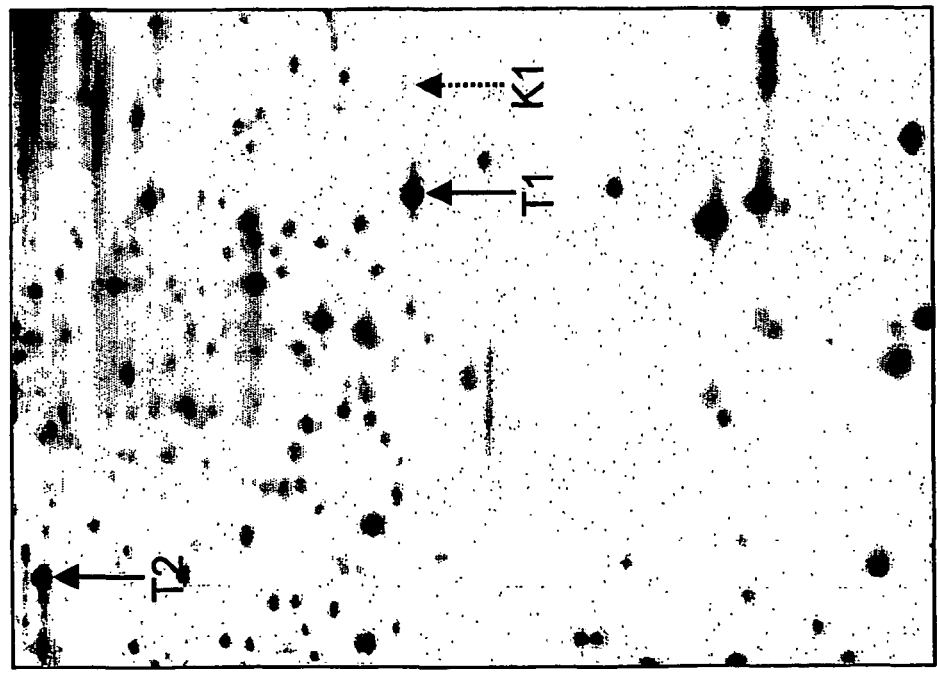
ink treated

SEQUENCE LISTING

<160> NUMBER OF SEQ ID NOS: 29

<210> SEQ ID NO 1
<211> LENGTH: 7
<212> TYPE: PRT
<213> ORGANISM: Aplysia

<400> SEQUENCE: 1

Asp Gly Glu Asp Ala Ala Val
1               5

<210> SEQ ID NO 2
<211> LENGTH: 9
<212> TYPE: PRT
<213> ORGANISM: Aplysia
<220> FEATURE:
<221> NAME/KEY: MOD_RES
<222> LOCATION: (1)..(1)
<223> OTHER INFORMATION: Asp can be Asp or Gln
<220> FEATURE:
<221> NAME/KEY: MOD_RES
<222> LOCATION: (3)..(3)
<223> OTHER INFORMATION: Ile can be Ile or Val
<220> FEATURE:
<221> NAME/KEY: MOD_RES
<222> LOCATION: (7)..(7)
<223> OTHER INFORMATION: Gln can be Gln or Arg
<220> FEATURE:
<221> NAME/KEY: MOD_RES
<222> LOCATION: (9)..(9)
<223> OTHER INFORMATION: Gln can be Gln or Pro

<400> SEQUENCE: 2

Asp Gly Ile Cys Arg Asn Gln Arg Gln
1               5

<210> SEQ ID NO 3
<211> LENGTH: 4
<212> TYPE: PRT
<213> ORGANISM: Aplysia

<400> SEQUENCE: 3

Phe Ala Asp Ser
1

<210> SEQ ID NO 4
<211> LENGTH: 8
<212> TYPE: PRT
<213> ORGANISM: Aplysia
<220> FEATURE:
<221> NAME/KEY: MOD_RES
<222> LOCATION: (5)..(5)
<223> OTHER INFORMATION: Ile can be Ile or Leu

<400> SEQUENCE: 4

Gly Pro Asp Gly Ile Val Ala Asp
1               5

<210> SEQ ID NO 5
<211> LENGTH: 7
<212> TYPE: PRT
<213> ORGANISM: Aplysia
<220> FEATURE:
<221> NAME/KEY: MOD_RES
<222> LOCATION: (6)..(6)
<223> OTHER INFORMATION: Lys can be Lys or Gln
<220> FEATURE:
<221> NAME/KEY: MOD_RES

```
<222> LOCATION: (7)..(7)
<223> OTHER INFORMATION: Ile can be Ile or Leu

<400> SEQUENCE: 5

Pro Gly Glu Val Ser Lys Ile
1               5

<210> SEQ ID NO 6
<211> LENGTH: 15
<212> TYPE: PRT
<213> ORGANISM: Aplysia

<400> SEQUENCE: 6

Ala Thr Gln Ala Tyr Ala Ala Val Arg Pro Ile Pro Ala Ser Lys
1               5                  10                  15

<210> SEQ ID NO 7
<211> LENGTH: 13
<212> TYPE: PRT
<213> ORGANISM: Aplysia

<400> SEQUENCE: 7

Asp Ser Gly Leu Asp Ile Ala Val Glu Tyr Ser Asp Arg
1               5                  10

<210> SEQ ID NO 8
<211> LENGTH: 12
<212> TYPE: PRT
<213> ORGANISM: Aplysia

<400> SEQUENCE: 8

Gly Asp Val Pro Tyr Asp Leu Ser Pro Glu Glu Lys
1               5                  10

<210> SEQ ID NO 9
<211> LENGTH: 442
<212> TYPE: DNA
<213> ORGANISM: Aplysia
<220> FEATURE:
<221> NAME/KEY: CDS
<222> LOCATION: (1)..(441)
<220> FEATURE:
<221> NAME/KEY: misc_feature
<222> LOCATION: (1)..(15)
<223> OTHER INFORMATION: sequence of the oligonucleotide

<400> SEQUENCE: 9
```

| | | | | | | | | | | | | | | | | |
|---|---|---|---|---|---|---|---|---|---|---|---|---|---|---|---|---|
| caa | gac | ggg | gaa | gac | aag | gag | ttt | gac | gga | gaa | atc | gtc | agc | gtc | aga | 48 |
| Gln | Asp | Gly | Glu | Asp | Lys | Glu | Phe | Asp | Gly | Glu | Ile | Val | Ser | Val | Arg | |
| 1 | | | | 5 | | | | | 10 | | | | | 15 | | |
| gtg | ctg | aag | gcg | ttc | ggc | aag | cct | ggc | tac | ggt | tac | aag | cag | ccc | tcg | 96 |
| Val | Leu | Lys | Ala | Phe | Gly | Lys | Pro | Gly | Tyr | Gly | Tyr | Lys | Gln | Pro | Ser | |
| | | 20 | | | | | 25 | | | | | 30 | | | | |
| tgc | aag | gaa | ggc | aag | gac | tac | gtg | agc | agc | ggc | agc | gtt | ctt | cac | gtg | 144 |
| Cys | Lys | Glu | Gly | Lys | Asp | Tyr | Val | Ser | Ser | Gly | Ser | Val | Leu | His | Val | |
| | 35 | | | | | 40 | | | | | 45 | | | | | |
| ctg | cag | tgt | gcc | ggc | ttc | ttc | gag | gtg | tgc | tac | gag | gag | agg | atc | acc | 192 |
| Leu | Gln | Cys | Ala | Gly | Phe | Phe | Glu | Val | Cys | Tyr | Glu | Glu | Arg | Ile | Thr | |
| | 50 | | | | | 55 | | | | | 60 | | | | | |
| acc | cag | cca | gcc | acg | act | gtc | gct | gca | gca | gag | gta | caa | tgc | aaa | aag | 240 |
| Thr | Gln | Pro | Ala | Thr | Thr | Val | Ala | Ala | Ala | Glu | Val | Gln | Cys | Lys | Lys | |
| 65 | | | | | 70 | | | | | 75 | | | | | 80 | |
| ttc | atc | gca | acc | cac | aaa | ttg | gag | gag | act | gtt | gat | gga | agg | atc | gtc | 288 |
| Phe | Ile | Ala | Thr | His | Lys | Leu | Glu | Glu | Thr | Val | Asp | Gly | Arg | Ile | Val | |
| | | | | 85 | | | | | 90 | | | | | 95 | | |

```
agc atc gag ctt gtc cag aga ctg aag aaa caa tcc gga tac ggt cca      336
Ser Ile Glu Leu Val Gln Arg Leu Lys Lys Gln Ser Gly Tyr Gly Pro
        100                 105                 110 agt ggc ggt tct ggt tat ggc aac ggt cat ggt caa aga ccc ggt tac      384
Ser Gly Gly Ser Gly Tyr Gly Asn Gly His Gly Gln Arg Pro Gly Tyr
            115                 120                 125 gga tac ggt tct ggt agt gga agt ggc tac gcc ccc aga gga gga tac      432
Gly Tyr Gly Ser Gly Ser Gly Ser Gly Tyr Ala Pro Arg Gly Gly Tyr
    130                 135                 140 aac cca aaa g                                                         442
Asn Pro Lys
145

<210> SEQ ID NO 10
<211> LENGTH: 147
<212> TYPE: PRT
<213> ORGANISM: Aplysia

<400> SEQUENCE: 10

Gln Asp Gly Glu Asp Lys Glu Phe Asp Gly Glu Ile Val Ser Val Arg
1               5                   10                  15

Val Leu Lys Ala Phe Gly Lys Pro Gly Tyr Gly Tyr Lys Gln Pro Ser
            20                  25                  30

Cys Lys Glu Gly Lys Asp Tyr Val Ser Ser Gly Ser Val Leu His Val
        35                  40                  45

Leu Gln Cys Ala Gly Phe Phe Glu Val Cys Tyr Glu Glu Arg Ile Thr
    50                  55                  60

Thr Gln Pro Ala Thr Thr Val Ala Ala Glu Val Gln Cys Lys Lys
65                  70                  75                  80

Phe Ile Ala Thr His Lys Leu Glu Glu Thr Val Asp Gly Arg Ile Val
                85                  90                  95

Ser Ile Glu Leu Val Gln Arg Leu Lys Lys Gln Ser Gly Tyr Gly Pro
            100                 105                 110

Ser Gly Gly Ser Gly Tyr Gly Asn Gly His Gly Gln Arg Pro Gly Tyr
        115                 120                 125

Gly Tyr Gly Ser Gly Ser Gly Ser Gly Tyr Ala Pro Arg Gly Gly Tyr
    130                 135                 140

Asn Pro Lys
145

<210> SEQ ID NO 11
<211> LENGTH: 462
<212> TYPE: DNA
<213> ORGANISM: Aplysia
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (58)..(58)
<223> OTHER INFORMATION: n is a, c, g, or t
<220> FEATURE:
<221> NAME/KEY: misc_feature
<222> LOCATION: (73)..(73)
<223> OTHER INFORMATION: n is a, c, g, or t
<220> FEATURE:
<221> NAME/KEY: misc_feature
<222> LOCATION: (132)..(132)
```

```
<223> OTHER INFORMATION: n is a, c, g, or t
<220> FEATURE:
<221> NAME/KEY: misc_feature
<222> LOCATION: (150)..(150)
<223> OTHER INFORMATION: n is a, c, g, or t
<220> FEATURE:
<221> NAME/KEY: misc_feature
<222> LOCATION: (182)..(182)
<223> OTHER INFORMATION: n is a, c, g, or t
<220> FEATURE:
<221> NAME/KEY: misc_feature
<222> LOCATION: (220)..(220)
<223> OTHER INFORMATION: n is a, c, g, or t
<220> FEATURE:
<221> NAME/KEY: misc_feature
<222> LOCATION: (254)..(254)
<223> OTHER INFORMATION: n is a, c, g, or t
<220> FEATURE:
<221> NAME/KEY: misc_feature
<222> LOCATION: (317)..(317)
<223> OTHER INFORMATION: n is a, c, g, or t
<220> FEATURE:
<221> NAME/KEY: misc_feature
<222> LOCATION: (338)..(338)
<223> OTHER INFORMATION: n is a, c, g, or t
<220> FEATURE:
<221> NAME/KEY: misc_feature
<222> LOCATION: (445)..(462)
<223> OTHER INFORMATION: sequence of the oligonucleotide

<400> SEQUENCE: 11
taccgccccc gccaccactn tngcaccagc agaaccaacc tgcgagaagc tgtccgtntg      60
gttcaacgtg ganaagaaat tcgaaggttc cagaatcgtg agtttcaagc tcatccgcct    120
gttcaacagg tncaagaagt gcaagaaagn ccagtattcc gtgtctggcg atgatgagga    180
cncattcgtt gtcagtggtt gttctggcgt gttccaggtn tgctacgaag aacaaacggc    240
gcccgctaca accnccacag aagccccgaa gccagagcca agaagaccca agaggaaaaa    300
tttcccaatc aaatttngta aacactgatg ggttaatntg acgaccagtg cgtctgcgaa    360
agaatcatgt tatggttcat gatgtcatgc tcttaatata ggttgtaacg tttaacgcga    420
tacagacatt aaaactcatt gttcaaaaaa aaaaaaaaaa aa                       462

<210> SEQ ID NO 12
<211> LENGTH: 154
<212> TYPE: PRT
<213> ORGANISM: Aplysia
<220> FEATURE:
<221> NAME/KEY: MOD_RES
<222> LOCATION: (1)..(154)
<223> OTHER INFORMATION: Xaa = unknown amino acid or STOP codon
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (44)..(44)
<223> OTHER INFORMATION: Xaa can be any naturally occurring amino acid
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: misc_feature
```

```
<222> LOCATION: (58)..(59)
<223> OTHER INFORMATION: Xaa can be any naturally occurring amino acid
<220> FEATURE:
<221> NAME/KEY: misc_feature
<222> LOCATION: (61)..(61)
<223> OTHER INFORMATION: Xaa can be any naturally occurring amino acid
<220> FEATURE:
<221> NAME/KEY: misc_feature
<222> LOCATION: (74)..(74)
<223> OTHER INFORMATION: Xaa can be any naturally occurring amino acid
<220> FEATURE:
<221> NAME/KEY: misc_feature
<222> LOCATION: (85)..(85)
<223> OTHER INFORMATION: Xaa can be any naturally occurring amino acid
<220> FEATURE:
<221> NAME/KEY: misc_feature
<222> LOCATION: (106)..(107)
<223> OTHER INFORMATION: Xaa can be any naturally occurring amino acid
<220> FEATURE:
<221> NAME/KEY: misc_feature
<222> LOCATION: (112)..(113)
<223> OTHER INFORMATION: Xaa can be any naturally occurring amino acid
<220> FEATURE:
<221> NAME/KEY: misc_feature
<222> LOCATION: (132)..(132)
<223> OTHER INFORMATION: Xaa can be any naturally occurring amino acid
<220> FEATURE:
<221> NAME/KEY: misc_feature
<222> LOCATION: (136)..(136)
<223> OTHER INFORMATION: Xaa can be any naturally occurring amino acid
<220> FEATURE:
<221> NAME/KEY: misc_feature
<222> LOCATION: (144)..(144)
<223> OTHER INFORMATION: Xaa can be any naturally occurring amino acid

<400> SEQUENCE: 12

Tyr Arg Pro Arg His His Xaa Xaa Thr Ser Arg Thr Asn Leu Arg Glu
1               5                   10                  15

Ala Val Arg Xaa Val Gln Arg Gly Xaa Glu Ile Arg Arg Phe Gln Asn
            20                  25                  30

Arg Glu Phe Gln Ala His Pro Pro Val Gln Gln Xaa Gln Glu Val Gln
        35                  40                  45

Glu Xaa Pro Val Phe Arg Val Trp Arg Xaa Xaa Gly Xaa Ile Arg Cys
    50                  55                  60

Gln Trp Leu Phe Trp Arg Val Pro Gly Xaa Leu Arg Arg Thr Asn Gly
65                  70                  75                  80

Ala Arg Tyr Asn Xaa His Arg Ser Pro Glu Ala Arg Ala Lys Lys Thr
                85                  90                  95

Gln Glu Glu Lys Phe Pro Asn Gln Ile Xaa Xaa Thr Leu Met Gly Xaa
            100                 105                 110

Xaa Asp Asp Gln Cys Val Cys Glu Arg Ile Met Leu Trp Phe Met Met
        115                 120                 125

Ser Cys Ser Xaa Tyr Arg Leu Xaa Arg Leu Thr Arg Tyr Arg His Xaa
    130                 135                 140

Asn Ser Leu Phe Lys Lys Lys Lys Lys
145                 150

<210> SEQ ID NO 13
<211> LENGTH: 153
<212> TYPE: PRT
<213> ORGANISM: Aplysia
<220> FEATURE:
<221> NAME/KEY: MOD_RES
<222> LOCATION: (1)..(153)
<223> OTHER INFORMATION: Xaa = unknown amino acid or STOP codon
<220> FEATURE:
<221> NAME/KEY: misc_feature
<222> LOCATION: (7)..(7)
```

```
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (44)..(44)
<223> OTHER INFORMATION: Xaa can be any naturally occurring amino acid
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: misc_feature
<222> LOCATION: (61)..(61)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid
<220> FEATURE:
<221> NAME/KEY: misc_feature
<222> LOCATION: (85)..(85)
<223> OTHER INFORMATION: Xaa can be any naturally occurring amino acid
<220> FEATURE:
<221> NAME/KEY: misc_feature
<222> LOCATION: (106)..(106)
<223> OTHER INFORMATION: Xaa can be any naturally occurring amino acid
<220> FEATURE:
<221> NAME/KEY: misc_feature
<222> LOCATION: (109)..(109)
<223> OTHER INFORMATION: Xaa can be any naturally occurring amino acid
<220> FEATURE:
<221> NAME/KEY: misc_feature
<222> LOCATION: (113)..(113)
<223> OTHER INFORMATION: Xaa can be any naturally occurring amino acid
<220> FEATURE:
<221> NAME/KEY: misc_feature
<222> LOCATION: (127)..(127)
<223> OTHER INFORMATION: Xaa can be any naturally occurring amino acid
<220> FEATURE:
<221> NAME/KEY: misc_feature
<222> LOCATION: (138)..(138)
<223> OTHER INFORMATION: Xaa can be any naturally occurring amino acid

<400> SEQUENCE: 13

Thr Ala Pro Ala Thr Thr Xaa Ala Pro Ala Glu Pro Thr Cys Glu Lys
 1               5                  10                  15

Leu Ser Xaa Trp Phe Asn Val Xaa Lys Lys Phe Glu Gly Ser Arg Ile
            20                  25                  30

Val Ser Phe Lys Leu Ile Arg Leu Phe Asn Arg Xaa Lys Lys Cys Lys
        35                  40                  45

Lys Xaa Gln Tyr Ser Val Ser Gly Asp Asp Glu Asp Xaa Phe Val Val
    50                  55                  60

Ser Gly Cys Ser Gly Val Phe Gln Xaa Cys Tyr Glu Glu Gln Thr Ala
65                  70                  75                  80

Pro Ala Thr Thr Xaa Thr Glu Ala Pro Lys Pro Glu Pro Arg Arg Pro
                85                  90                  95

Lys Arg Lys Asn Phe Pro Ile Lys Phe Xaa Lys His Xaa Trp Val Asn
            100                 105                 110

Xaa Thr Thr Ser Ala Ser Ala Lys Glu Ser Cys Tyr Gly Ser Xaa Cys
        115                 120                 125

His Ala Leu Asn Ile Gly Cys Asn Val Xaa Arg Asp Thr Asp Ile Lys
    130                 135                 140
```

```
Thr His Cys Ser Lys Lys Lys Lys
145                 150

<210> SEQ ID NO 14
<211> LENGTH: 153
<212> TYPE: PRT
<213> ORGANISM: Aplysia
<220> FEATURE:
<221> NAME/KEY: MOD_RES
<222> LOCATION: (1)..(153)
<223> OTHER INFORMATION: Xaa = unknown amino acid or STOP codon
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (44)..(44)
<223> OTHER INFORMATION: Xaa can be any naturally occurring amino acid
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: misc_feature
<222> LOCATION: (60)..(60)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid
<220> FEATURE:
<221> NAME/KEY: misc_feature
<222> LOCATION: (84)..(84)
<223> OTHER INFORMATION: Xaa can be any naturally occurring amino acid
<220> FEATURE:
<221> NAME/KEY: misc_feature
<222> LOCATION: (105)..(105)
<223> OTHER INFORMATION: Xaa can be any naturally occurring amino acid
<220> FEATURE:
<221> NAME/KEY: misc_feature
<222> LOCATION: (112)..(113)
<223> OTHER INFORMATION: Xaa can be any naturally occurring amino acid
<220> FEATURE:
<221> NAME/KEY: misc_feature
<222> LOCATION: (133)..(133)
<223> OTHER INFORMATION: Xaa can be any naturally occurring amino acid

<400> SEQUENCE: 14

Pro Pro Pro Pro Xaa Xaa His Gln Gln Asn Gln Pro Ala Arg Ser
1               5                   10                  15

Cys Pro Xaa Gly Ser Thr Trp Xaa Arg Asn Ser Lys Val Pro Glu Ser
            20                  25                  30

Xaa Val Ser Ser Ser Ala Cys Ser Thr Gly Xaa Arg Ser Ala Arg
                35                  40                  45

Lys Xaa Ser Ile Pro Cys Leu Ala Met Met Arg Xaa His Ser Leu Ser
    50                  55                  60

Val Val Val Leu Ala Cys Ser Arg Xaa Ala Thr Lys Asn Lys Arg Arg
65                  70                  75                  80

Pro Leu Gln Xaa Pro Gln Lys Pro Arg Ser Gln Ser Gln Glu Asp Pro
```

-continued

```
                85                  90                  95
Arg Gly Lys Ile Ser Gln Ser Asn Xaa Val Asn Thr Asp Gly Leu Xaa
            100                 105                 110
Xaa Arg Pro Val Arg Leu Arg Lys Asn His Val Met Val His Asp Val
        115                 120                 125
Met Leu Leu Ile Xaa Val Val Thr Phe Asn Ala Ile Gln Thr Leu Lys
    130                 135                 140
Leu Ile Val Gln Lys Lys Lys Lys
145                 150

<210> SEQ ID NO 15
<211> LENGTH: 30
<212> TYPE: DNA
<213> ORGANISM: Aplysia
<220> FEATURE:
<221> NAME/KEY: misc_feature
<222> LOCATION: (8)..(28)

<400> SEQUENCE: 15
cgaactatcg acgttgtgtg gctgcattac                                       30

<210> SEQ ID NO 16
<211> LENGTH: 20
<212> TYPE: DNA
<213> ORGANISM: Aplysia brasiliana

<400> SEQUENCE: 16
tcgcggtcag gttcctggcg                                                  20

<210> SEQ ID NO 17
<211> LENGTH: 21
<212> TYPE: DNA
<213> ORGANISM: Artificial Sequence
<220> FEATURE:
<223> OTHER INFORMATION: oligonucleotide primer
<220> FEATURE:
<221> NAME/KEY: misc_feature
<222> LOCATION: (1)..(1)
<223> OTHER INFORMATION: n = poly T

<400> SEQUENCE: 17
ntcgacgttg tgtggctgca t                                                21

<210> SEQ ID NO 18
<211> LENGTH: 20
<212> TYPE: DNA
<213> ORGANISM: Aplysia

<400> SEQUENCE: 18
ctgggaattc caggaaagca                                                  20

<210> SEQ ID NO 19
<211> LENGTH: 20
<212> TYPE: DNA
<213> ORGANISM: Aplysia

<400> SEQUENCE: 19
tcgtggctgg acaccgagaa                                                  20

<210> SEQ ID NO 20
<211> LENGTH: 48
<212> TYPE: DNA
<213> ORGANISM: Artificial Sequence
<220> FEATURE:
```

<223> OTHER INFORMATION: oligonucleotide primer

<400> SEQUENCE: 20
cgaactatcg acgttgtgtg gctgcattac ttttttttt tttttttt        48

<210> SEQ ID NO 21
<211> LENGTH: 20
<212> TYPE: DNA
<213> ORGANISM: Artificial Sequence
<220> FEATURE:
<223> OTHER INFORMATION: oligonucleotide primer
<220> FEATURE:
<221> NAME/KEY: misc_feature
<222> LOCATION: (6)..(6)
<223> OTHER INFORMATION: M = A or C
<220> FEATURE:
<221> NAME/KEY: misc_feature
<222> LOCATION: (14)..(14)
<223> OTHER INFORMATION: N = desoxyinosin

<400> SEQUENCE: 21
tcggtmarga cggngaagac        20

<210> SEQ ID NO 22
<211> LENGTH: 5
<212> TYPE: PRT
<213> ORGANISM: Aplysia
<220> FEATURE:
<221> NAME/KEY: misc_feature
<222> LOCATION: (2)..(2)
<223> OTHER INFORMATION: Xaa can be any naturally occurring amino acid

<400> SEQUENCE: 22

Thr Xaa Gly Pro Ala
1               5

<210> SEQ ID NO 23
<211> LENGTH: 14
<212> TYPE: PRT
<213> ORGANISM: Aplysia

<400> SEQUENCE: 23

Tyr Gly Arg Lys Lys Arg Arg Gln Arg Arg Pro Pro Pro
1               5                   10

<210> SEQ ID NO 24
<211> LENGTH: 16
<212> TYPE: PRT
<213> ORGANISM: Aplysia

<400> SEQUENCE: 24

Arg Gln Ile Lys Ile Trp Phe Gln Asn Arg Arg Met Lys Trp Lys Lys
1               5                   10                  15

<210> SEQ ID NO 25
<211> LENGTH: 20
<212> TYPE: DNA
<213> ORGANISM: Aplysia

<400> SEQUENCE: 25
tcgcggtcag gttcctggcg        20

<210> SEQ ID NO 26
<211> LENGTH: 21

```
<212> TYPE: DNA
<213> ORGANISM: Artificial Sequence
<220> FEATURE:
<223> OTHER INFORMATION: oligonucleotide primer
<220> FEATURE:
<221> NAME/KEY: misc_feature
<222> LOCATION: (1)..(1)
<223> OTHER INFORMATION: n = poly T

<400> SEQUENCE: 26
ntcgacgttg tgtggctgca t                                      21

<210> SEQ ID NO 27
<211> LENGTH: 20
<212> TYPE: DNA
<213> ORGANISM: Aplysia

<400> SEQUENCE: 27
ctgggaattc caggaaagca                                        20

<210> SEQ ID NO 28
<211> LENGTH: 20
<212> TYPE: DNA
<213> ORGANISM: Aplysia

<400> SEQUENCE: 28
tcgtggctgg acaccgagaa                                        20

<210> SEQ ID NO 29
<211> LENGTH: 5
<212> TYPE: PRT
<213> ORGANISM: Aplysia
<220> FEATURE:
<221> NAME/KEY: MOD_RES
<222> LOCATION: (1)..(1)
<223> OTHER INFORMATION: Lys can be Lys or Gln

<400> SEQUENCE: 29

Lys Asp Gly Glu Asp
1               5
```

IDENTIFICATION OF A NEW CYTOTOXIC ACTIVITY FROM THE INK OF APLYSIA PUNCTATA

CROSS REFERENCE TO RELATED APPLICATION

This application is a 35 USC § 371 National Phase Entry Application from PCT/EP01/11837, filed Oct. 12, 2001, and designating the U.S.

Description

The present invention relates to novel proteins having cytotoxic activity derived from the sea hare *Aplysia*.

The sea hare *Aplysia* produces a pink-coloured ink, which has cytotoxic activity towards several eukaryotic cell lines. WO97/16457 discloses a partial sequence from an *Aplysia* protein, which allegedly has anti-tumor activity. Cyplasin L (558 aa, NCBI accession number 11967690) and cyplasin S (421 aa, 11967688; Petzelt and Werner, 2001, Cell Biology International, 25(2):A23) both include parts of sequences disclosed in WO 97/16457. Cyplasin S exhibits 95% sequence identity to cyplasin L. Cyplasin L is produced in the nidamental gland but neither in the ink gland (including the mantle region) nor in the opaline gland of *Aplysia punctata*. Thus, it is concluded that cyplasin is not a component of *Aplysia* ink and is not responsible for the cytotoxic activity of the *Aplysia* ink. A detailed description of *Aplysia* anatomy and a dissection guide can be found in the internet in Richard Fox, Invertebrate anatomy (1994).

Yamazaki et al. (FEBS Letters 198 (1986), 25–28) and Yamazaki ("Anti-tumor and anti-microbial glycoproteins from sea hares", in: Comparative Biochemistry and Physiology 105c (1993), 141–146) describe several cytotoxic factors from *Aplysia kurodai, Aplysia juliana* and *Dolabella auricularia* as well as from other sea organisms. No data are presented from *Aplysia punctata*.

Yamazaki et al. (1986), supra, describe the isolation and purification of a cytolytic factor, aplysianin-P from *A. kurodai*. Aplysianin-P gives a single protein bond of 60 kDa on SDS-polyacrylamide gel electrophoresis.

Yamazaki et al. (1989, Cancer Res. 49:3834–3838 have revealed the N-terminal sequence of aplysianin-P (Thr-X-Gly-Pro-Ala). In addition, they showed that the cytolytic effect of aplysianin-P can be inhibited by 50 mM N-acetyl neuraminic acid.

Yamazaki (1993) reviews 9 antitumor and antimicrobial glycoproteins from sea hares. The cytotoxic factors were purified according to standard methods. Further, the sensitivity of the cytotoxic activity against chemical and physical treatments (e.g. urea, periodate, heat, low pH, protease) was tested. The results for the individual cytotoxic factors, however, did not show any signficant difference; thus, these criteria are unsuitable for characterizing individual factors.

MacColl et al. (The Biological Bulletin 179 (1990)) describes a composition of the ink from *Aplysia californica*, particularly, the chromophoric components. Among the polypeptide components, a 61 kD protein is described which, however, has not been purified. Further, a characterization of cytotoxic factors is not described.

According to the present invention, the cytotoxic activity from the ink of *Aplysia punctata* was purified. The purified fraction contained a protein with an apparent molecular mass of about 60 kDa exhibiting a cytotoxic activity similar to the crude ink. The protein was analysed by peptide mass fingerprinting with MALDI-MS, internal sequencing with ESI-MS/MS and N-terminal sequencing.

Thus, a subject matter of the present invention is a polypeptide obtainable from *Aplysia* having a molecular mass of about 60±5 kDa as determined by SDS-PAGE. The polypeptide may be a substantially isolated and purified polypeptide, it should be noted, however, that it also may be present in a partially purified form, e.g. in a fraction of *Aplysia* ink. The polypeptide is obtainable from *Aplysia*, particularly, *A. punctata, A. brasiliana, A. californica, A. dactylomela, A. depilans, A. extraordinaria, A. juliana, A. cf. parvula, A. parvula, A. sagamiana* and *A. vaccaria*. Further, the invention also encompasses fragments of said polypeptide wherein the length of the fragment is preferably at least 6, more preferably at least 10 and most preferably at least 20 amino acids. In the following, the term "polypeptide" encompasses fragments as specified above.

The polypeptide of the present invention exhibits a selective cytotoxic activity towards eukaryotic and particular mammalian tumor cells, e.g. the human T cell line Jurkat E6 (ATCC TIB 152). Normal cells are much more resistant to the polypeptide than tumor cells. For example, subpopulations of PBMCs from healthy donors are insensitive to the polypeptide. The following tumor cell lines are highly sensitive to the polypeptide: Jurkat neo, Jurkat Bcl-2, CEM Neo, CEM Bcl-$x_L$, K562 (ATCC CCL-243), MCF-7 neo/MCF-7-Bcl-$x_L$ (breast adenocarcinoma), SKW-Neo/SKW-Bcl-2 (acute myeloid leukemia, AML), GLC4/GLC4-ADR (MDR tumor cells, obtained by selection with adriamycin; small cell lung cancer).

The cytotoxic activity of the present invention is insensitive to N-acetyl neuraminic acid.

The cytotoxic activity may be caused by the polypeptide per se and/or by a variant of said polypeptide and/or by a cofactor bound to said polypeptide. In the following the term "polypeptide" encompasses these embodiments.

In one embodiment of the present invention the polypeptide comprises an amino acid partial sequence selected from (a) Asp-Gly-Glu-Asp-Ala-Ala-Val and/or (SEQ ID NO.1)

(b) (Asp/Gln)-Gly-(Ile/Val)-Cys-Arg-Asn-(Gln/Arg)-Arg-(Gln/Pro). (SEQ ID NO.2)

Further the invention encompasses a fragment of said polypeptide, which fragment may or may not comprise the partial sequence given above. A polypeptide of this embodiment is the protein APL-1 from *A. punctata* or a fragment thereof.

In a further preferred embodiment the polypeptide comprises an amino acid sequence selected from (a) Phe-Ala-Asp-Ser, (SEQ ID NO.3)

(b) Gly-Pro-Asp-Gly-(Ile/Leu)-Val-Ala-Asp and/or (SEQ ID NO.4)

(c) Pro-Gly-Glu-Val-Ser-(Lys/Gln)-Ile/Leu). (SEQ ID NO.5)

By means of mass spectrometry further amino acid partial sequences

Ala-Thr-Gln-Ala-Tyr-Ala-Ala-Val-Arg-Pro-Ile-Pro-Ala-Ser-Lys, (SEQ ID NO.6)

Asp-Ser-Gly-Leu-Asp-Ile-Ala-Val-Glu-Tyr-Ser-Asp-Arg and (SEQ ID NO.7)

Gly-Asp-Val-Pro-Tyr-Asp-Leu-Ser-Pro-Glu-Glu-Lys (SEQ ID NO.8)

of a polypeptide of the invention could be identified.

The invention also encompasses a fragment of said polypeptide, which fragment may or may not comprise the partial sequence given above. Examples of polypeptides falling under this embodiment are the proteins APL-2, APL-3 and APL-4 obtainable from *A. punctata* or fragments thereof. These polypeptides have slight differences in the molecular weight, but having at least partially the same amino acid primary structure.

The amino acid sequences of the above polypeptides do not show any overlap with previously known amino acid sequences of cytotoxic factors from *Aplysia*, e.g. cyplasin S and cyplasin L (Petzelt und Werner (2001), supra); aplysianin A (Takamazu et al., FEBS Lett. 377 (1995), 373–376); achacin (Obara et al., Eur. J. Biochem. 209 (1992), 1–6).

In addition to the polypeptides having the amino acid sequences as given above, the invention encompasses further polypeptides comprising variants, e.g. amino acid sequence variants thereof. Amino acid sequence variants are obtainable by deletion, addition and/or substitution of one or several amino acids in the original sequence. Particularly, the term "variants" refers to amino acid sequences which differ in one or two amino acid residues from the amino acid partial sequences given above. Further, the term "variant" in this context describes any alteration of the cytotoxic polypeptide in size and/or in charge. The alterations may be due to transcriptional, translational and/or posttranslational modifications or to genetic manipulations on the nucleic acid level resulting in amino acid sequence variants.

The polypeptides of the present invention are obtainable by isolation from natural sources such as *Aplysia* and optionally fragmentation, e.g. by proteolytic enzymes such as trypsin. On the other hand, the polypeptides of the present invention are obtainable by chemical synthesis or recombinant DNA methods.

Preferably, the polypeptide of the present invention is resistant against proteases such as pronase, trypsin or proteinase K. This resistance may be caused by modifications such as carbohydrate or lipid residues. Alternatively, the resistance may be caused by the binding of factors to the polypeptide. This resistance against proteolytic cleavage may be caused via a mechanism which may be used for a general protection of proteins or oligopeptides against digestion. This might be of great importance for oral medicaments.

A further aspect of the present invention is a nucleic acid encoding a polypeptide as specified above. The nucleic acid may be a single stranded or double stranded nucleic acid, e.g. a DNA, RNA or a nucleic acid analog such as a peptide nucleic acid (PNA). Preferably, the nucleic acid has a length of at least 10 nucleotides, more preferably of at least 18 nucleotides and most preferably of at least 25 nucleotides. The nucleic acid is obtainable from natural sources e.g. from *Aplysia* by extraction of RNA, construction of cDNA libraries and screening of the library using degenerated oligonucleotides which were deduced from the peptide sequences described above. The nucleic acid is further obtainable by RT-PCR using RNA extracted from *Aplysia* and oligo-dT-primers or degenerated primers. On the other hand, the nucleic acid is obtainable by chemical synthesis.

A preferred example of such a nucleic acid encoding a cytotoxic polypeptide comprises (a) the partial nucleotide sequence encoding the corresponding partial amino acid sequence as disclosed in Example 6 (SEQ ID NO.9/10 and/or 11/12/13/14), (b) a sequence corresponding to the sequence of (a) within the scope of degeneracy of the genetic code or (c) a sequence hybrididzing under stringent conditions with the sequence of (a) and/or (b). Hybridization under stringent conditions preferably means that after washing for 1 h with 1×SSC and 0.1% SDS at 55° C., preferably at 62° C. and more preferably at 68° C., particularly after washing for 1 h with 0.2×SSC and 0.1% SDS at 55° C., preferably at 62° C. and more preferably at 68° C., a hybridization signal is detected.

In a preferred embodiment of the invention the nucleic acid is operatively linked to an expression control sequence, e.g. a sequence which is capable of directing expression in a suitable host cell, e.g. a prokaryotic or eukaryotic host cell. The expression control sequence usually comprises a promoter and optionally operator or enhancer sequences which enable a transcription of the nucleic acid operatively linked thereto. Furthermore, the expression control sequence may contain a translation signal, e.g. a ribosome binding sequence.

The nucleic acid of the present invention may be a recombinant vector which contains in addition usual vector sequences such as an origin of replication, a selection marker gene and/or a cloning site. Examples of suitable vectors such as plasmids, phages or viral vectors are known to the skilled person and are described e.g. in Sambrook et al., Molecular Cloning, A Laboratory Manual (2nd ed. 1998), Cold Spring Harbor, Laboratory Press.

A further aspect of the present invention is a recombinant cell transformed or transfected with a nucleic acid as described above. The recombinant cell may be a prokaryotic cell, e.g. a gram-negative prokaryotic cell such as *E. coli* or a eukaryotic cell, e.g. an insect cell or a vertebrate cell such as a mammalian cell. Techniques for transforming or transfecting host cells with nucleic acids are known to the skilled person and e.g. described in Sambrook et al., supra.

Still a further subject matter of the present invention is an antibody directed against a polypeptide as described above. The antibody may be a polyclonal or monoclonal antibody or a recombinant antibody, e.g. a chimeric antibody, a humanized antibody or a single chain antibody. Furthermore, the antibody may be an antibody fragment containing the antigen-binding site of the antibody, e.g. a Fab fragment.

The antibody may be obtained by immunizing suitable experimental animals with an *Aplysia* polypeptide or a partial fragment thereof or a peptide antigen optionally coupled to a suitable macromolecular carrier according to known protocols, e.g. by techniques which are described in Borrebaeck, Carl A. K. (Ed.), Antibody engineering (1992) or Clark, Mike (Ed.), Protein engineering of antibody molecules for prophylactic and therapeutic applications in man (1993). By techniques for producing hybridoma cell lines according to Köhler and Milstein monoclonal antibodies may be obtained.

The cytotoxic activity of the polypeptide may be used to locally destroy tissues and/or selectively kill cells in tissues. The polypeptide may be used to locally destroy tumours and/or selectively kill tumour cells in healthy tissues. Therefore the polypeptide may be coupled to a targeting molecule which specifically directs the polypeptide to or into certain cells. The targeting molecule may bind to a cell surface receptor which enables the uptake of the polypeptide into the cell. Targeting may alternatively be achieved by administering the polypeptide via suitable carriers, e.g. liposomes or virions which cause uptake of the polypeptide into specific target cells.

Possible targeting molecules are proteins or peptides. For example, antibodies or fragments thereof may be bound to the polypeptide. Bivalent, bispecific antibodies recognizing the polypeptide and a cellular surface structure may be used for targeting. The polypeptide may be fused to antibody or antibody fragments or to recombinant antibodies like single chain antibodies for targeting. Thus, the molecule may be a fusion protein and may be produced by genetically engineered microorganisms. Further, the polypeptide may be fused to a small peptide which recognizes cell surface structures for targeting, e.g. the membrane translocation signal of HIV-Tat (Tyr-Gly-Arg-Lys-Lys-Arg-Arg-Gln-Arg-Arg-Arg-Pro-Pro-Pro) or of *Drosophila* antennapedia homeo-domain (Arg-Gln-Ile-Lys-Ile-Trp-Phe-Gln-Asn-Arg-Arg-Met-Lys-Trp-Lys-Lys). Fusion proteins containing these peptides are selectively uptaken by certain cell types.

The present invention also relates to a pharmaceutical composition comprising as an active agent the polypeptide, the nucleic acid, the recombinant cell or the antibody as specified above. Further, the composition may further comprise pharmaceutically acceptable carriers, diluents or adjuvants. The pharmaceutical composition may be used for the diagnosis and therapy of hyperproliferative diseases, particularly in the diagnosis or therapy of tumors, e.g. leukemias, carcinomas, sarcomas and melanomas.

The polypeptides of the present invention are also suitable for identifying novel targets for the development of pharmaceutical agents, particularly anti-tumor agents. Thus, the present invention also relates to a method for determining targets of a polypeptide as described above comprising the steps:
(a) contacting the polypeptide with a biological sample,
(b) determining interactions between the polypeptide and a target substance contained in the sample and
(c) identifying or characterizing the target substance.

The biological sample may be a cell, a cell extract or cellular components or organelles or isolated molecules, e.g. proteins. The interaction between the polypeptide and a substance contained in the sample may be a direct interaction, e.g. the polypeptide binds directly to a substance, e.g. a cellular target or receptor. On the other hand, the method allows also the determination of indirect interactions, wherein the substance is a cellular target affected by the polypeptide via a one- or multi-step signal transduction pathway. The indirect interaction may include the intracellular and/or extracellular release of reactive oxygen species, especially $H_2O_2$.

For example, targets of the polypeptide may be identified by modifications of cellular components, particularly proteins, which occur due to the treatment of the sample with the polypeptide. 'Modification' or 'modified' in this context describes the alteration of a protein in a given cellular compartment or in the extracellular space or in vitro. The protein may be changed in the size or in the charge or in the size and the charge. These changes may be due to transcriptional (e.g. splicing), translational and/or posttranslational (e.g. glycosylation and/or proteolysis) variations. Furthermore, modification includes translocation of the protein. 'Translocation' in this context describes differences in the localisation of a protein in compartments of cells treated with the cytotoxic activity or apoptosis-induced compared with the compartments of non-treated or non-induced cells.

The target substance, which is identified and/or characterized by the method as described above, may be used for the development of new pharmaceutical agents, e.g. by known high-throughput screening procedures which may be cellular screening procedures or molecular based screening procedures. In our context, characterization is the analysis of the chemical composition of the substance. Identification is the assignment of a target substance to its biological function.

Characterization can be performed by enzymatic digestion and mass fingerprinting. Thus, the target substance can be characterized by the pattern of masses of the fragments of the substance. In case the target substance is a peptide or polypeptide, characterization can further be performed by at least partial sequencing, for instance by mass spectrometry, e.g. ESI-MS/MS and/or Edman degradation.

The target substance may be a surface exposed molecule which is bound by the polypeptide/toxin. Surface exposed molecules of target cells might be labelled by standard techniques using radiolabelling or cross-linking of biotin to these proteins. The target substance then might be identified by generating blocking antibodies which bind the substance and prevent binding of the polypeptide/toxin. The target substance might also be identified by co-precipitation while bound to the polypeptide/toxin using antibodies directed against the polypeptide/toxin. The target substance might be detected by autoradiography or labelled streptavidin.

The targets and/or pattern of targets obtained by the method of the present invention for determining targets is different from the pattern of proteins modified during apoptosis.

The target may be thioredoxin peroxidase 2, (Topspot No. 4_504, Swissprot No. Q06830, NCBI No. 548453), 60S ribosomal protein P0 (3_300, 12654583 or 45066667), unidentified protein (4_62), Hsp-60 (N-term, 1_372, 14603309), stathmin (5_6, 5031851), Rho GDI 2 (3_192, P52566, 1707893), RNA binding regulatory subunit (O14805, 12720028), hnRNP C1/C2 (4758544), proteasome subunit beta type 1 (P20618, 130853), pre-mRNA cleavage factor Im (4_325, 5901926), proteasome subunit alpha type 7 (O14818, 12643540), U2 small nuclear ribonucleoprotein A' (P09661, 134094), GAP SH3 binding protein (5031703), DNA replication licensing factor MCM4 (P33991, 1705520), thioredoxin peroxidase 1 (3_255, P32119, 2507169), 40S ribosomal protein S21 (P35265, 464710), 40S ribosomal protein S12 (P25398, 133742), phosphoglycerate mutase 1 (4_138,P18669, 130348), HCC-1 protein (13940310), HnRNP A2/B1 (4_285,4504447/14043072), IMP dehydrogenase 2 (2_708,P12268,124419), hnRNP A/B (14724990) or proteins exhibiting a similar activity or involved in a similar signal transduction pathway. The internet address of the Topspot database is http://www-.mpiib-berlin.mpg.de/2D-PAGE.

Preferably, the target is a protein characterized by masses of peptide fragments obtainable by enzymatic digestion and peptide mass fingerprinting as listed in Table 2b and 3b.

In a particularly preferred embodiment, the target is GAP SH3 binding protein. GAP SH3 binding protein or fragments thereof can be used to generate diagnostic tools such as cleavage specific antibodies or phages or other tools useful for large scale screening. A nucleic acid sequence encoding the GAP-SH3 binding protein or a part thereof, e.g. the gene, the cDNA or a portion thereof, can be used to develop DNA-Chips or other DNA- or RNA-based screening devises (PCR, RT-PCR) to screen cells or tissues for the differences in the mRNA levels of the identified genes.

GAP SH3 protein or fragments thereof can be used to screen drugs which activate or inhibit GAP SH3 binding protein activity. This activity may be modification of the activity of Ras-GAP which modifies the activity of the ras-oncoprotein or other GTPases. The activity may be the RNA-binding or RNAse activity elicited by the modification of GAP SH3 binding protein after treatment with the *Aplysia punctata* factor of the present invention. This activity may be any activity elicited by the modification of the protein during treatment with the *Aplysia punctata* factor of the present invention. For example, this activity may be the binding to ubiquitin C-terminal hydrolase related polypeptide (UCHRP) or related proteins. A consequence of binding to UCHRP or related proteins may be the modification of cell differentiation in tumor genesis. Thus, GAP SH3 binding protein and binding partners might play an important role in tumor formation and metastasis formation. Alternatively, this activity may be the binding of GAP SH3 binding protein (dimerisation, multimerisation) which might be a prerequisite for a possible function of GAP SH3 binding protein in tumor genesis and metastasis formation.

GAP SH3 binding protein is therefore potentially involved in the growth control of cells. Tumors can overexpress or lack GAP SH3 binding protein or produce a modified GAP SH3 binding protein. Tumors can be defective in the RNA-modifying activity of GAP SH3 binding protein. Tumors can be defective of or constitutively bind interacting proteins like UCHRP or related proteins or GAP SH3 binding protein. Signals transduced via UCHRP or related proteins or GAP SH3 binding protein dimers or multimers or any interaction protein might trigger tumor genesis or metastasis formation. Drugs which interfere with constitutive GAP SH3 binding protein activity or which activate GAP SH3 binding protein activity or which interfere with binding or interacting proteins are useful for therapy of such diseases.

Other preferred targets are factors involved in the pathways generating reactive oxygen species (ROS), especially hydrogen peroxide ($H_2O_2$) or superoxide anions, which are activated by the polypeptide of the present invention. $H_2O_2$ is generated by dismutation of superoxide anions ($O_2^-$) or by peroxisomal enzymes independent of the production of superoxide anions. The major source for superoxide anions are the mitochondria or the endoplasmatic reticulum (ER). Other sources are the NADPH oxidase or the xanthine oxidase. The factors involved in $H_2O_2$ and/or $O_2^-$ generation or nucleic acids encoding such factors or parts thereof may be useful as diagnostics, e.g. prognostic markers, and/or to develop drugs which may activate or inhibit these factors.

Other preferred targets are factors involved in the pathways detoxifying ROS. Detoxification occurs by reducing $H_2O_2$ to $H_2O$ by thioredoxin peroxidases, glutathione peroxidases or catalases. The polypeptide of the present invention may activate or inhibit these factors involved in $H_2O_2$ detoxification.

Degenerative diseases like Alzheimer's and Parkinson's disease are characterised by excessive ROS production of the affected tissue. Drugs which either activate $H_2O_2$ detoxification or inhibit $H_2O_2$ production may be used for therapy of degenerative diseases like Alzheimer's or Parkinson's disease. Since thioredoxin peroxidases 1 and 2 have been shown to be overexpressed in cells at risk for diseases related to ROS toxicity including degenerative diseases like Alzheimer's and Parkinson's disease (Butterfield et al., 1999, *Antioxidants & Redox Signalling*, 1, 385–402), the targets obtainable by the method of the present invention for determining targets, e.g. thioredoxin peroxidases 1 and 2 and other factors involved in ROS metabolism (especially $H_2O_2$ metabolism) might be important targets for the development of drugs for treatment of degenerative diseases like Alzheimer's and Parkinson's disease.

Fast growing tumor cells produce more ROS and thus require an efficient $H_2O_2$ detoxification system. Drugs which either activate $H_2O_2$ production or which interfere with $H_2O_2$ detoxification may be used for therapy of proliferative diseases like tumors. Since thioredoxin peroxidases 1 and 2 have been shown to be overexpressed in tumor cells (Butterfield et al. 1999, *Antioxidants & Redox Signaling*, 1, 385–402), the targets obtainable by the method of the present invention for determining targets, e.g. thioredoxin peroxidases 1 and 2 and other factors involved in ROS metabolism (especially $H_2O_2$ metabolism) might be important targets for the development of drugs for treatment of proliferative diseases like tumors.

An important negative control of the potential aggressive function of natural killer (NK) cells seems to be the formation of $H_2O_2$ by monocytes, macrophages and granulocytes (Mellqvist, Blood 2000, 96 (5), 1961–1968). NK-cells encountering $H_2O_2$ are inhibited in their lytic activity, are made resistant to IL-2 activation and undergo apoptosis/ necrosis.

NK-cells have been shown to protect against malignant cells in chronic myelogenous leukemia (CML), but their number and inducibility is reduced during the progression of the disease. This reduction and dysfunction is due to the production of $H_2O_2$ by CML-cells (Mellqvist, Blood 2000, 96 (5), 1961–1968). Any therapy providing CML-patients with ROS-hyposensitive NK-cells therefore would be of great benefit. The targets described above could be used to modulate the $H_2O_2$ sensitivity of NK-cells or to inhibit the $H_2O_2$ production of malignant cells, e.g. CML-cells.

Arteriosclerosis with its progression to heart disease, stroke and peripheral vascular disease continues to be the leading cause of death in all western civilisations. Enhanced ROS-production (via endothelial NADPH-oxidase) is required and sufficient to generate the pathologic phenotype (Meyer, FEBS Letters 2000, 472, 1–4). Therefore, targets mediating the effect of $H_2O_2$ are useful to develop new drugs for treatment of arteriosclerosis and the associated diseases like heart disease, stroke and other vascular diseases. These targets are suitable to detoxify $H_2O_2$ and/or to block the $H_2O_2$ induced signalling pathways.

Furthermore, targets may be any factor involved in a pathway leading to blockage and/or by-passing of caspases.

Thus, the present invention relates to pharmaceutical agents which may act upon cellular receptors and/or components of the signal transduction pathways activated or inhibited by the *Aplysia* polypeptide or parts thereof.

While not wishing to be bound by theory, preliminary results show that the cytotoxic effect mediated by the polypeptides of the invention is different from known necrotic or apoptotic processes. Prior to cell death, the cells shrink. More particularly, shrinkage of the nuclei (after 2–3 h incubation) and the whole cells (after 10 h) is observed. The cell membrane becomes permeable. DNA fragmentation and forming of apoptotic bodies is not observed. Thus the polypeptides of the invention might be involved in cell volume regulation, and they may specifically act (directly or indirectly via a signal transduction pathway) upon ion channels, most probably upon the volume-regulated anion channels (VRAC, ORCC), or upon the cell volume regulatory $K^+$ channels Kv1.3. Thus, a further aspect of the present invention is the use of the polypeptides of the invention as specific ion channel modulators, e.g. blockers or openers for therapy, diagnosis or research.

For example, the pharmaceutic compositions of the invention are suitable for the manufacture of cytotoxic agents which are active against apoptosis-resistant cells, e.g. for the treatment of apoptosis-resistant hyperproliferation diseases, e.g. tumours.

The administration of the pharmaceutic compositions may be combined with the administration of further cytotoxic agents.

Further, the present invention shall be explained in more detail by the following figures, tables and examples.

Legends to the Figures and Tables:

FIG. 1: SDS-PAGE of the crude ink and the purified fractions
  A: Coomassie stained gel of the crude ink (T1) and the molecular mass marker (M; Masses from top in kDa: 205; 120; 84; 52.2; 36.3; 30.2). Proteins analysed by MALDI-MS are indicated.
  B: Silver stained gel of the crude ink (T1) the active fractions from the gel filtration FF9 and FF12 and the active fraction from the MonoQ anion exchange column. Note that APL-3 is the only protein which correlates with the cytotoxic activity. The larger protein in AF15 has been identified as purification artefact.

FIG. 2: MALDI-MS spectrum of a tryptic digest of APL-1.

Figure 3:
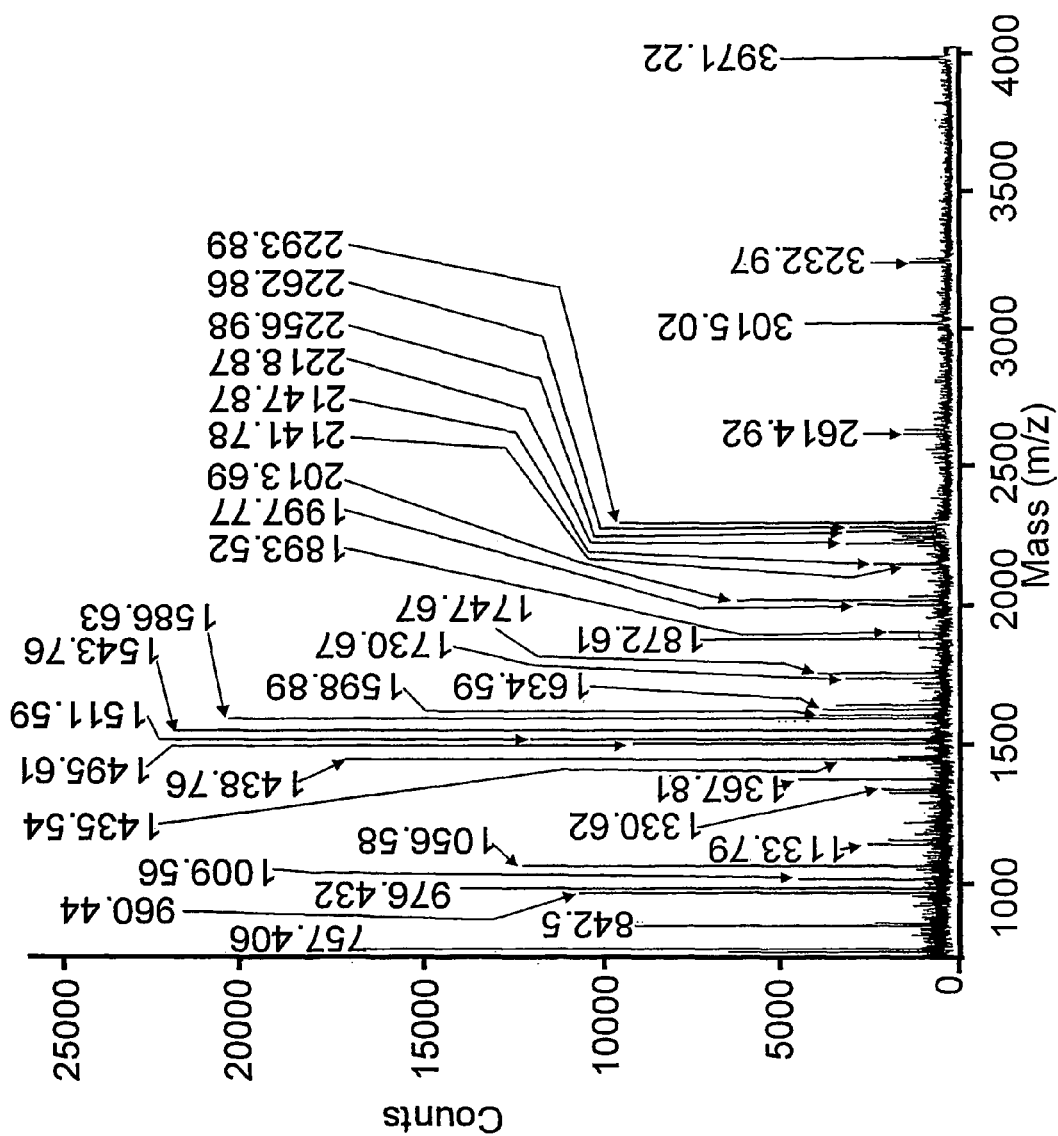

FIG. 3: MALDI-MS spectrum of a tryptic digest of APL-3.

Figure 4:
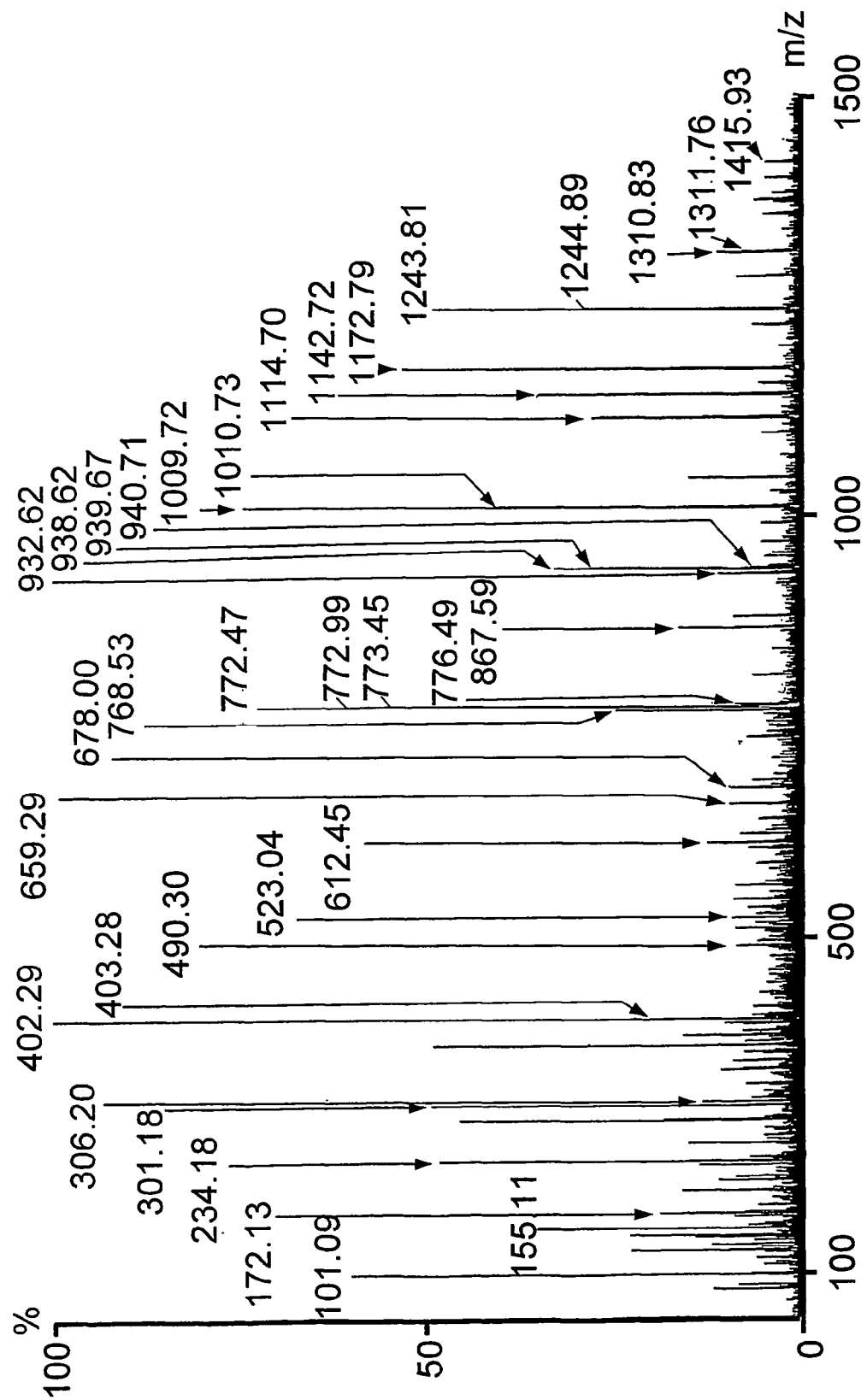

FIG. 4: ESI-MS/MS of the tryptic fragment with the mono protonated mass 1543.8 Da of APL-3.

Figure 5:
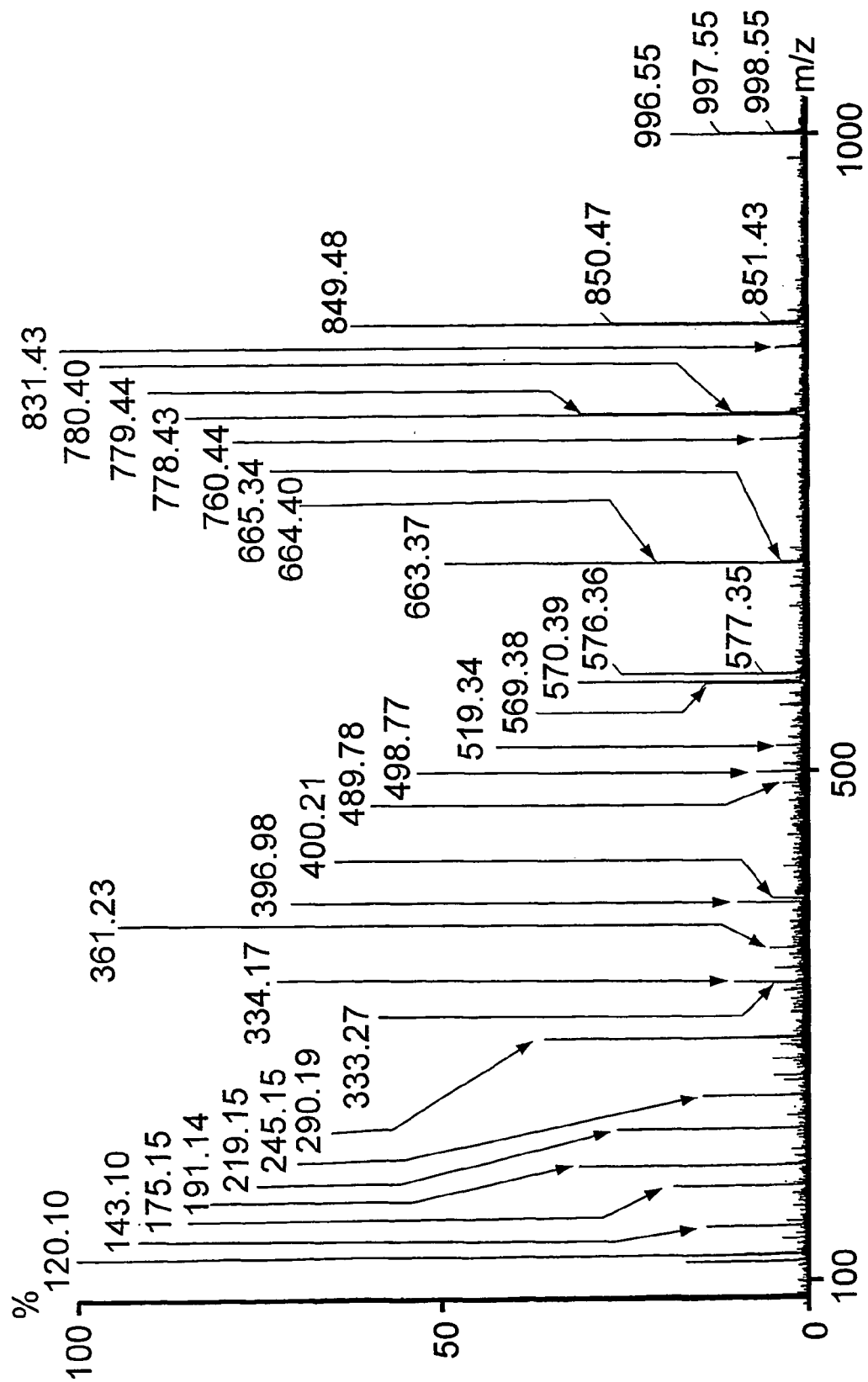

FIG. 5: ESI-MS/MS of the tryptic fragment with the mono protonated mass 1137.8 Da of APL-1.

Figure 6:
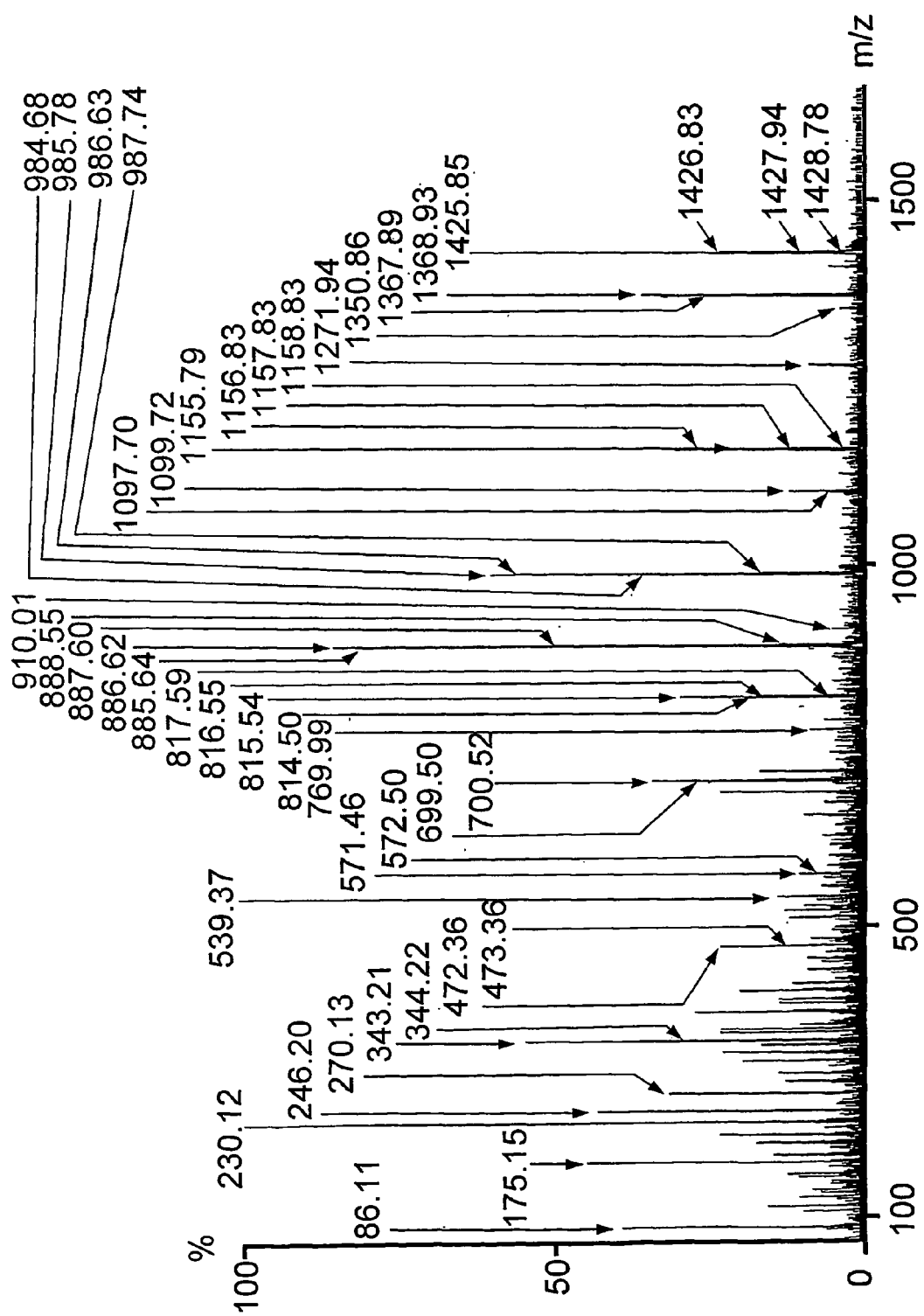

FIG. 6: ESI-MS/MS of the tryptic fragment with the mono protonated mass 1765.6 Da of APL-1.

Figure 7:
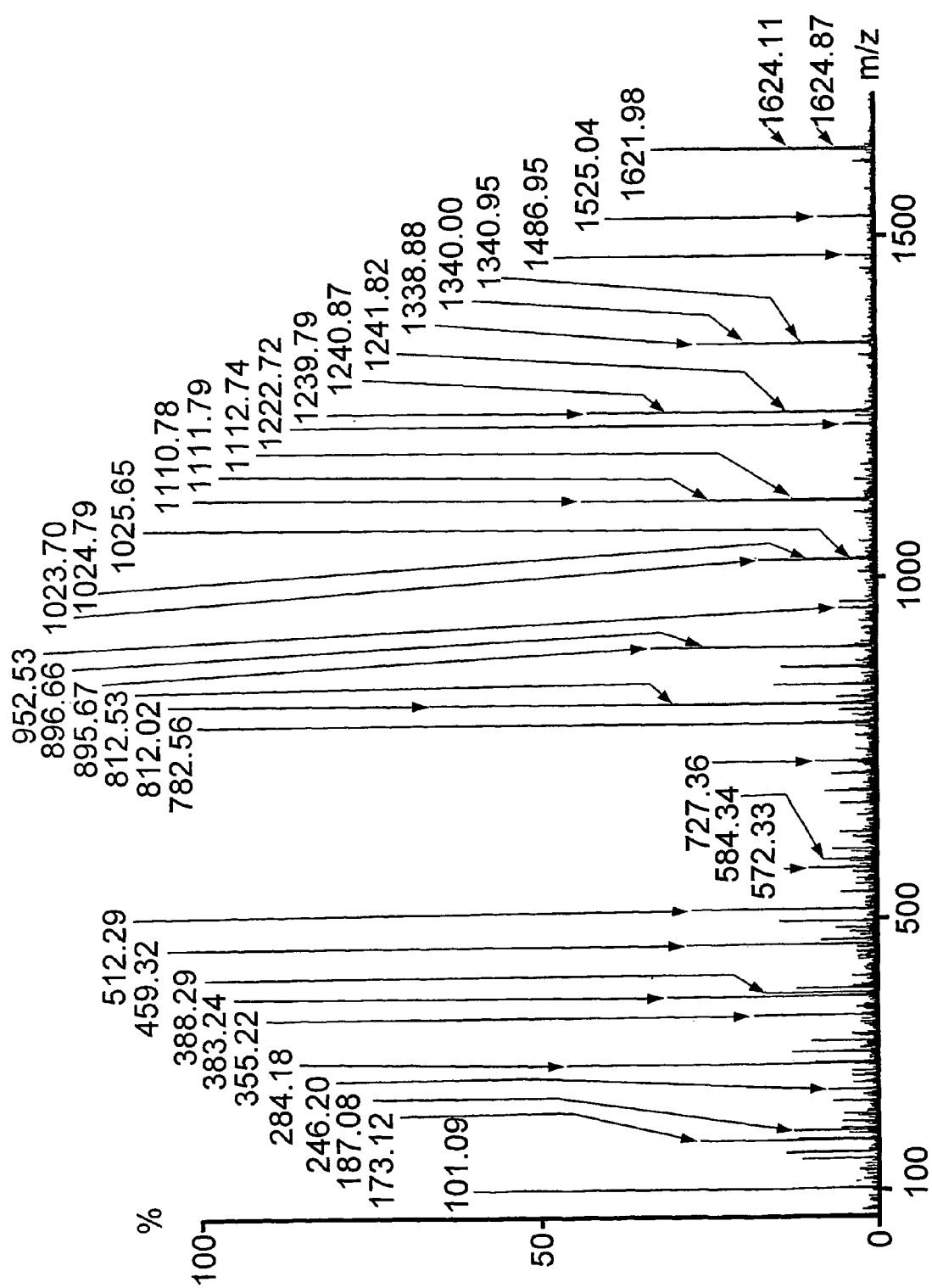

FIG. 7: ESI-MS/MS of the tryptic fragment with the mono protonated mass 1921.5 Da of APL-1.

FIG. 8: Jurkat T cells were treated for 6 h (A, C, E, G) or 8 h (B, D, F) with either PBS (A, B), 10 µg/ml cycloheximide (C, D) to induce apoptosis (Gottlieb R A, Nordberg J, Skowronski E, Babior B M., Proc. Natl. Acad. Sci. USA 1996, 93(2):654–8; Slee E A, Keogh S A, Martin S J., Cell Death Differ. 2000, 7(6):556–65), *Aplysia* ink (E, F) or a high potassium HEPES buffer (10 mM HEPES, 140 mM K, 5 mM NaCl, 2 mM $MgCl_2$, 2 mM $CaCl_2$) to induce necrosis (G). Note that apoptotic cells fragment, necrotic cells swell whereas ink-treated cells shrink without significant fragmentation.

Figure 9:
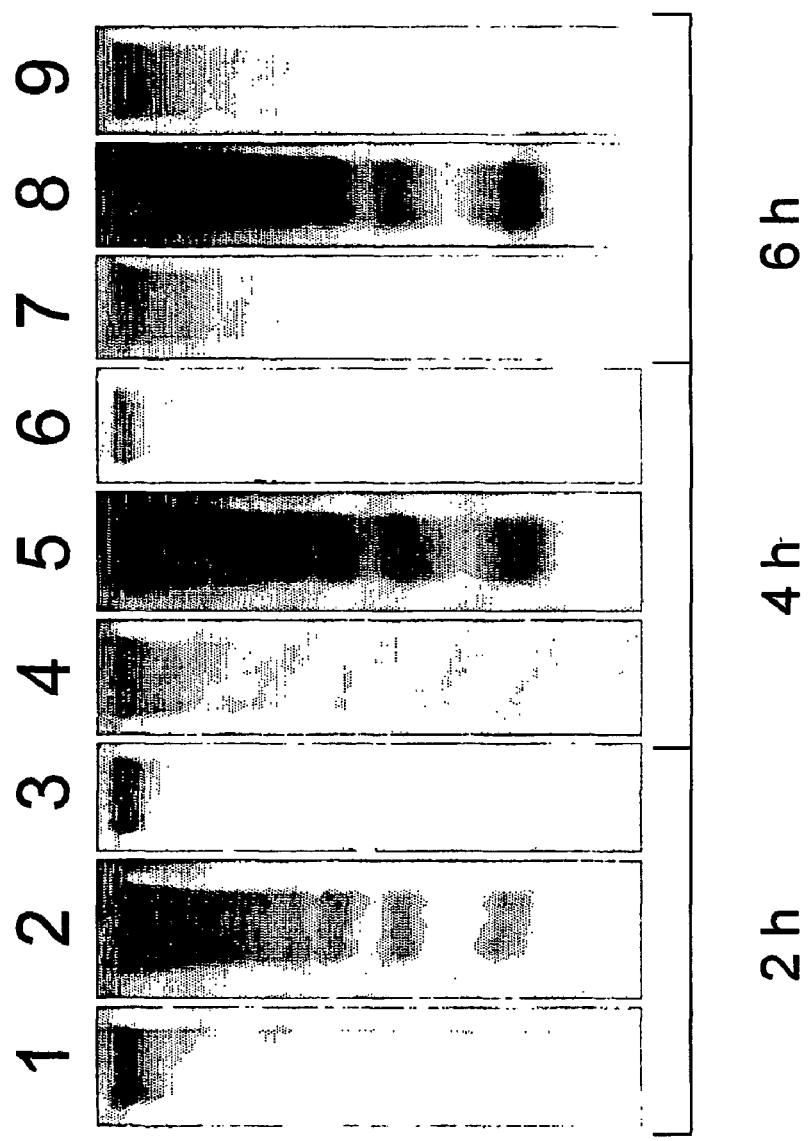

FIG. 9: DNA-fragmentation assay of apoptotic and ink-treated cells. Jurkat T cells were incubated for 2 (1–3), 4 (4–6) or 6 (7–9) h with control buffer (1, 4, 7), 10 µg/ml cycloheximide to induce apoptosis (2, 5, 8) or ink (3, 6, 9). Note that ink treated cells do not fragment their DNA as it is typical for apoptotic cells.

Figure 10:
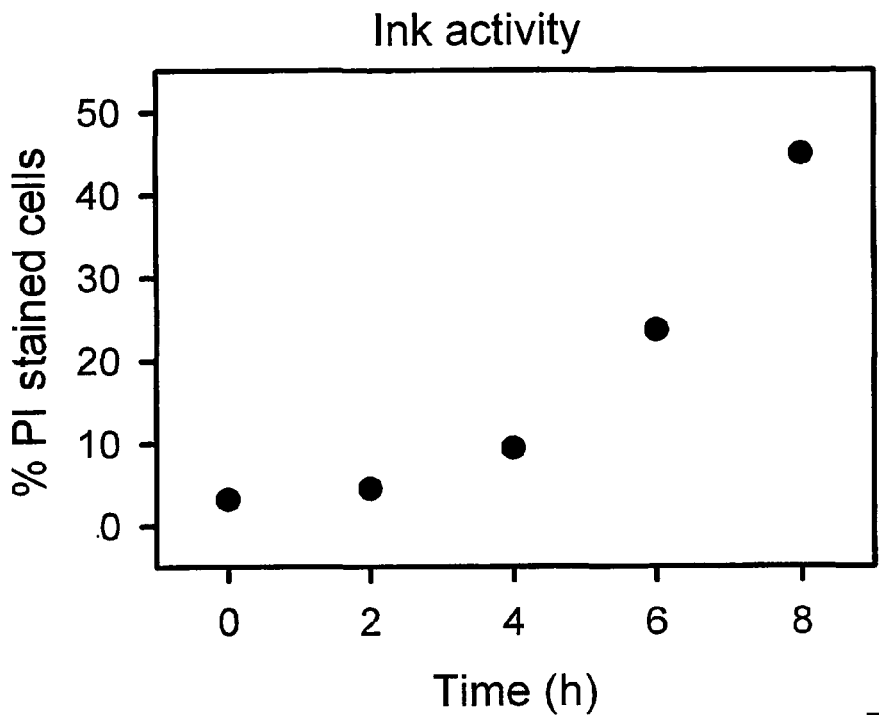

FIG. 10: Time course of propidium iodide uptake upon ink treatment. Jurkat T cells were treated with ink for the indicated times and the uptake of propidium iodide (PI) as indicator for an increase in permeability of the plasma membrane was measured by FACS analysis.

Figure 11:
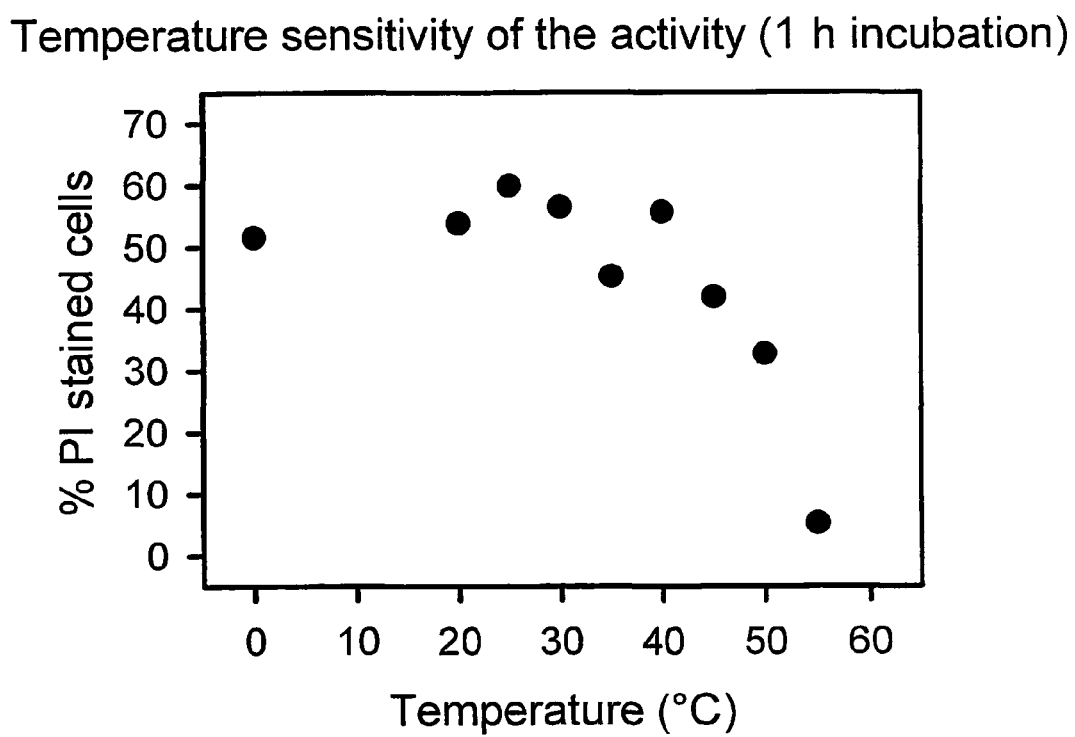

FIG. 11: Heat sensitivity of the cytotoxic activity. Ink was incubated for 1 h at the indicated temperature and the cytotoxic activity was measured by treatment of Jurkat T cells for 8 h. The decrease in propidium iodide uptake (see FIG. 10) indicates the loss of cytotoxic activity above 50° C.

Figure 12:
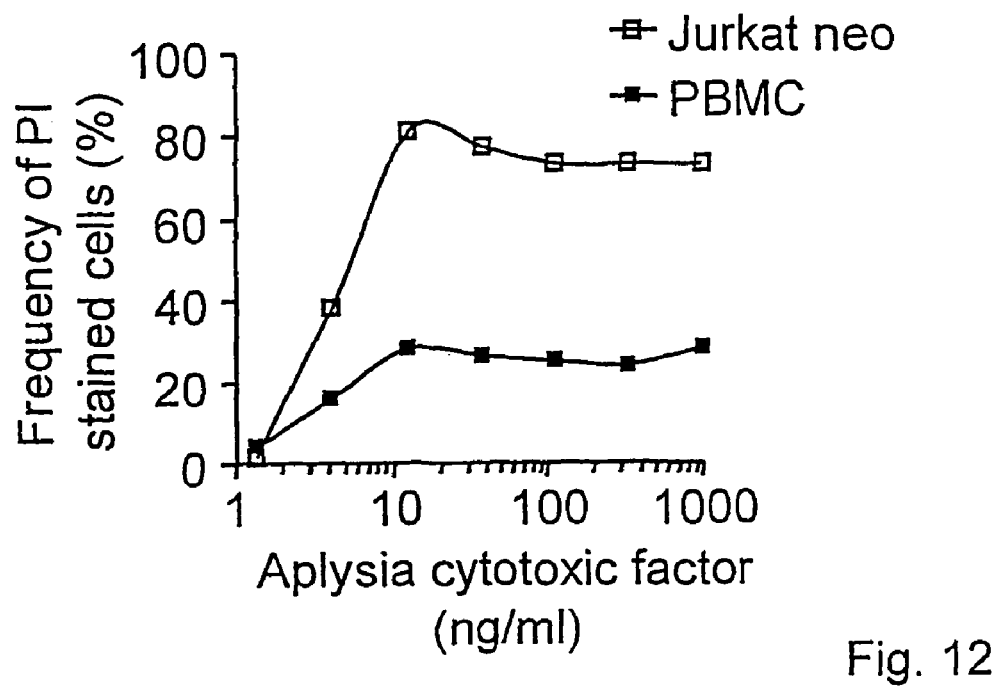

FIG. 12: Incubation of Jurkat neo cells and PBMCs from healthy donors with purified *Aplysia* cytotoxic activity (dose response curves). The frequency of PI stained cells gives the fraction of dead cells.

Figure 13:
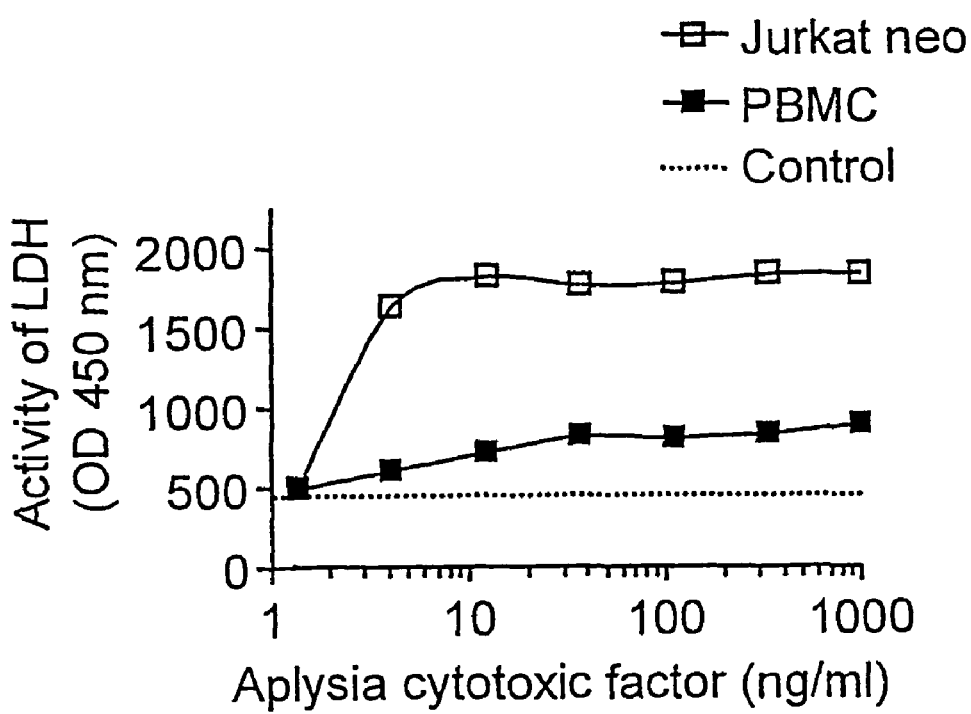

FIG. 13: Incubation of Jurkat neo cells and PBMCs from healthy donors with purified *Aplysia* cytotoxic activity (dose response curves). The amount of LDH activity in the supernatant is proportional to the number of dead cells. The dotted line indicates the basal LDH activity (control without cytotoxic activity).

Figure 14:
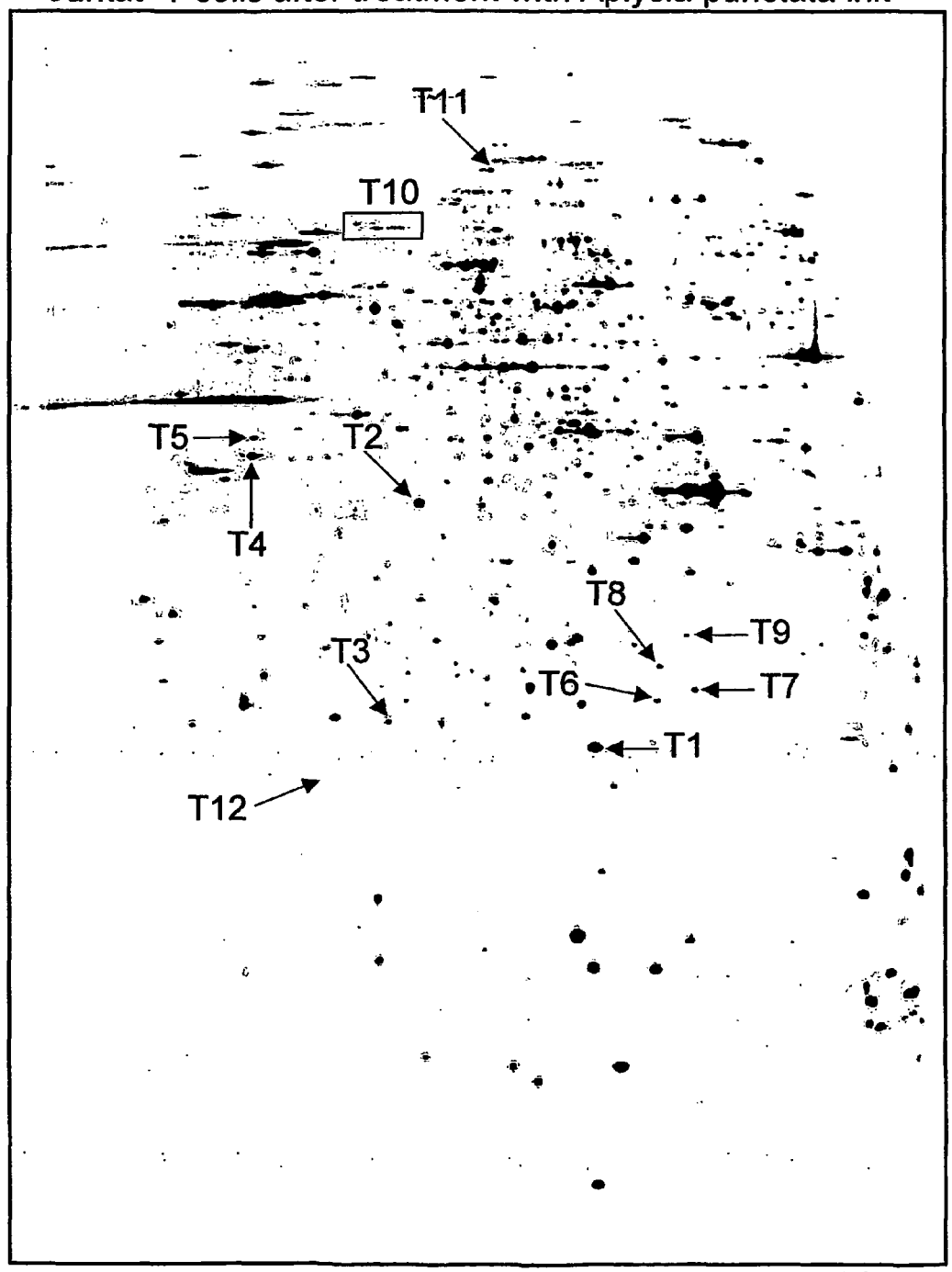

FIG. 14: 2-DE gel of total cell lysate of Jurkat T cells treated with *Aplysia punctata* ink. The spots T1 to T12 were modified by treatment with *Aplysia punctata* ink.

Figure 15:
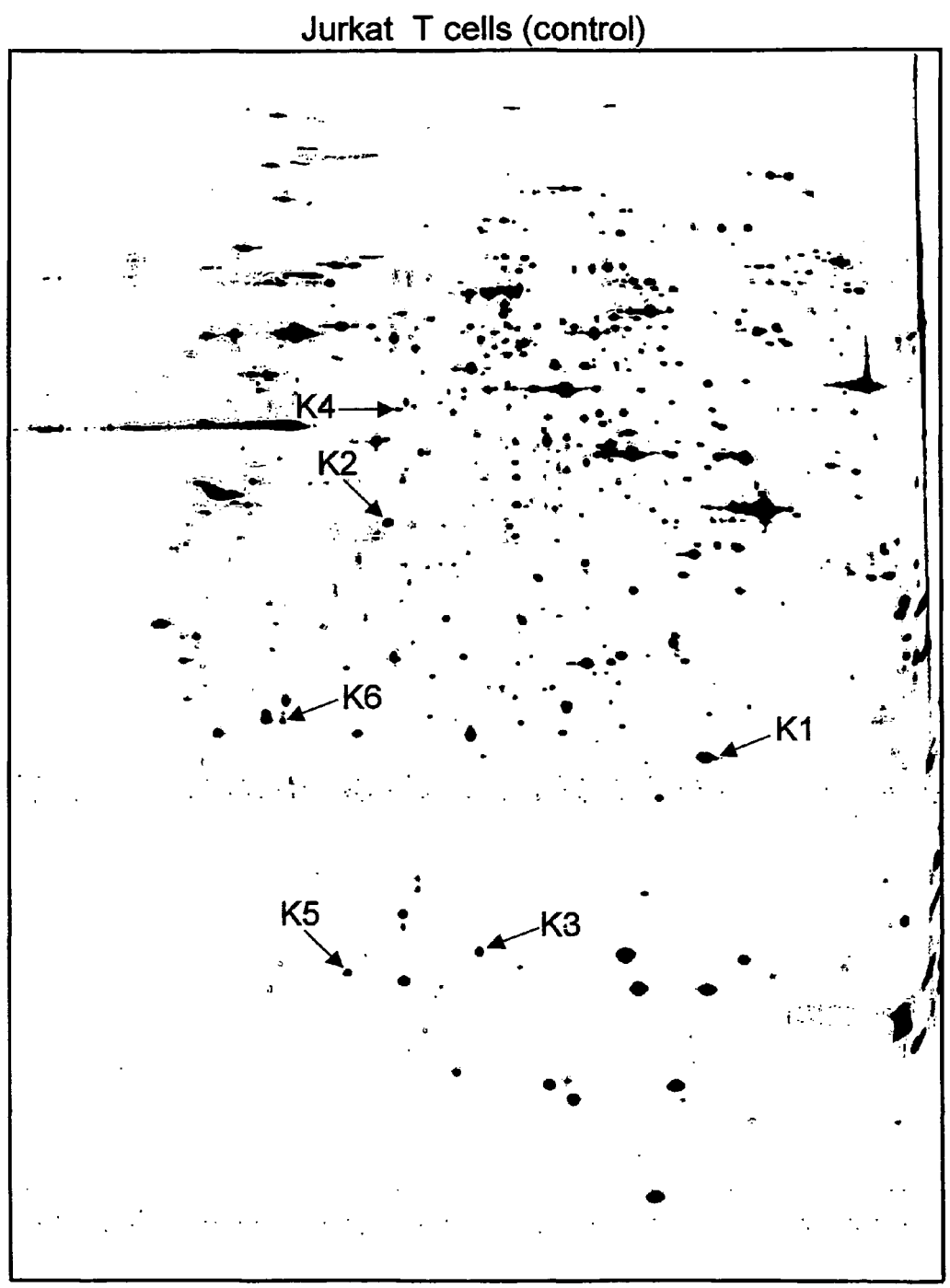

FIG. 15: 2-DE gel of total cell lysate of Jurkat T cells (control). The spots K1 to K6 were modified by treatment with *Aplysia punctata* ink.

Figure 16:
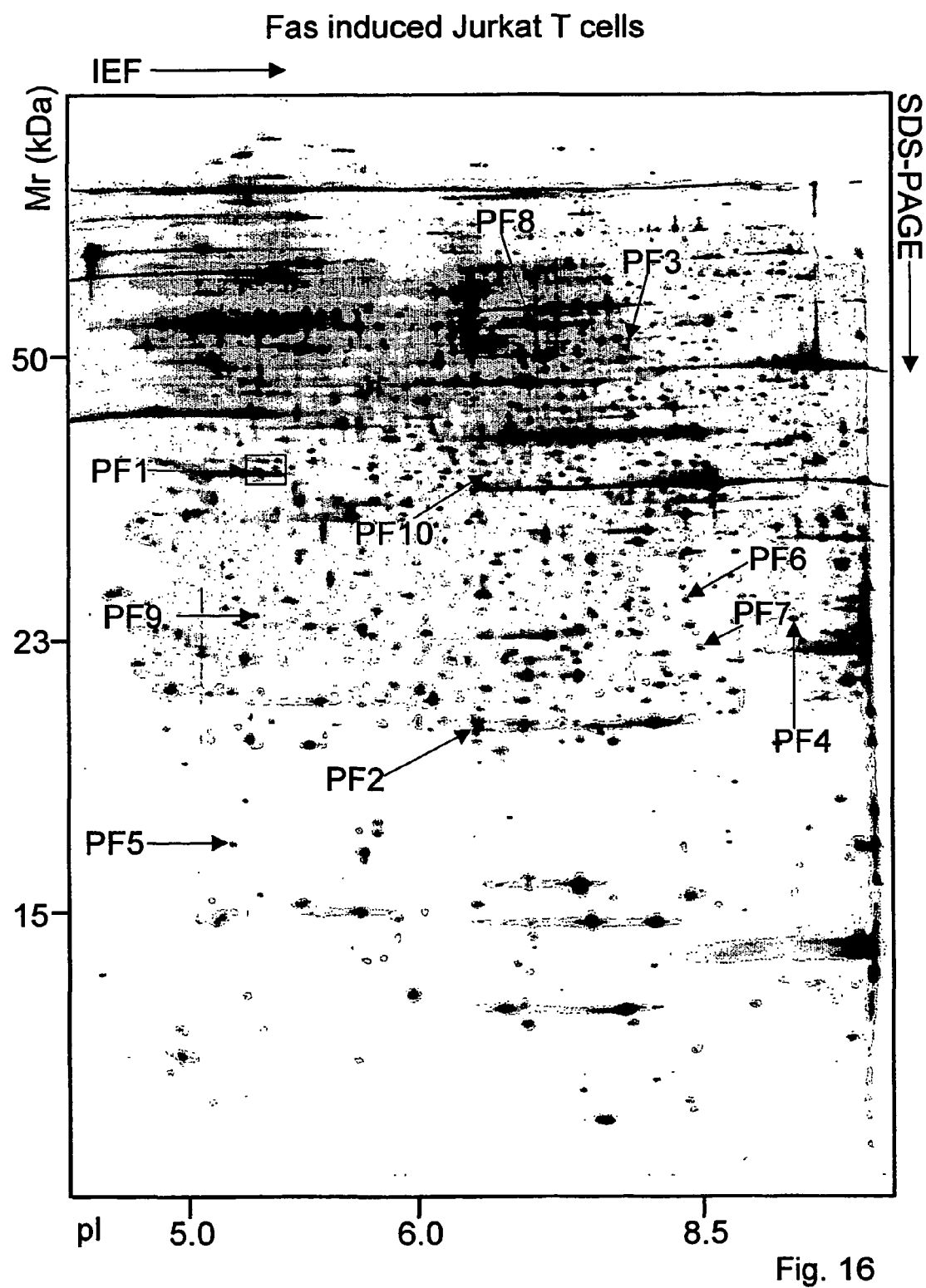

FIG. 16: 2-DE gel of total cell lysate of Fas induced Jurkat T cells. The spots PF1 to PF10 were modified during apoptosis.

Figure 17:
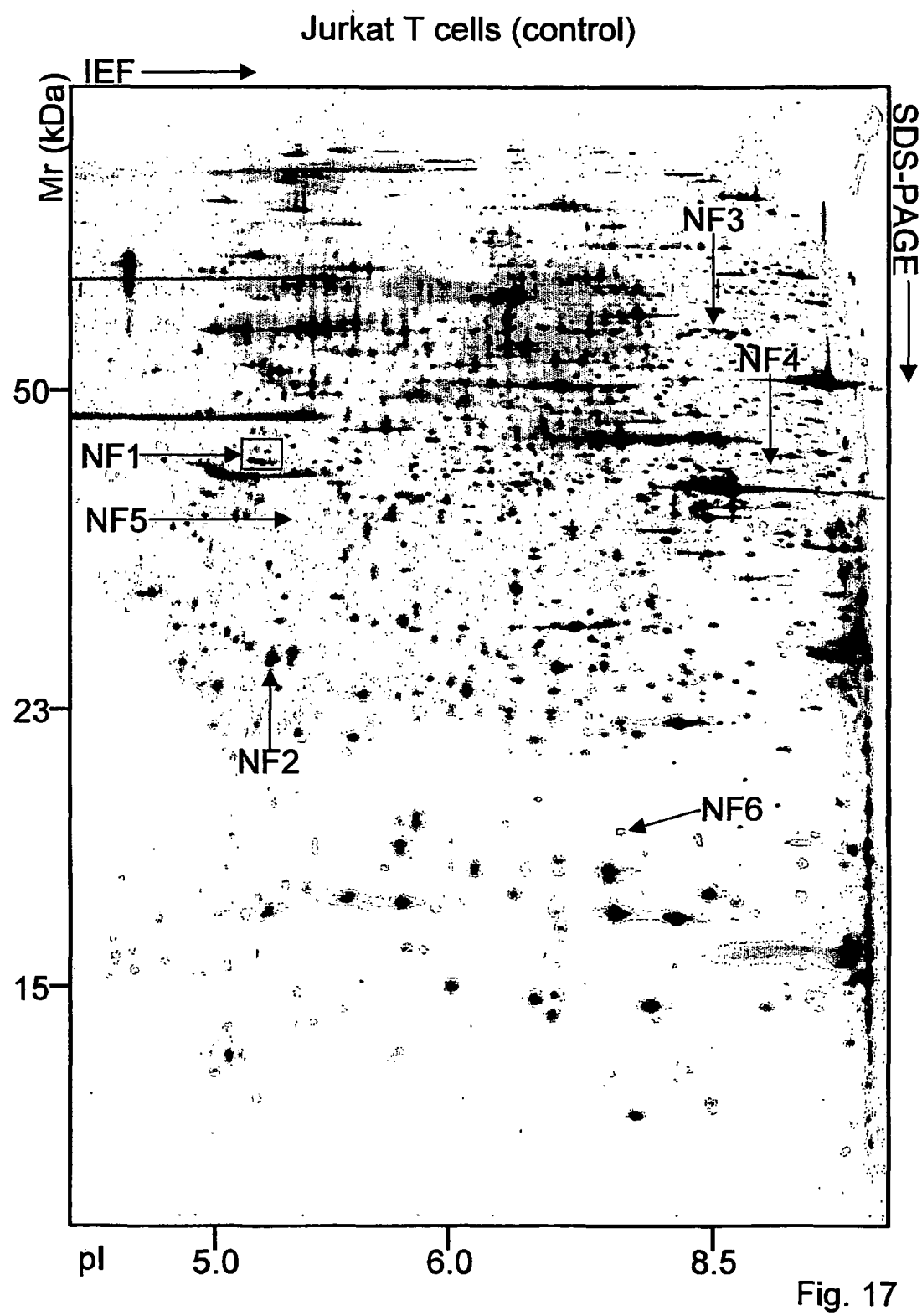

FIG. 17: 2-DE gel of total cell lysate of Jurkat T cells (control). The spots NF1 to NF6 were modified during apoptosis.

FIG. 18: Comparison of 2-DE gels of total cell lysate of Jurkat T cells treated with *A. punctata* ink and 500 µM $H_2O_2$.

T1 denotes the thioredoxin peroxidase 2 (cf. FIG. 14). K1 denotes the position of thioredoxin peroxidase 2 under control conditions (dotted arrow, cf. FIG. 15). T2 denotes the 60 S ribosomal protein P0 (cf. FIG. 14).

Figure 19:
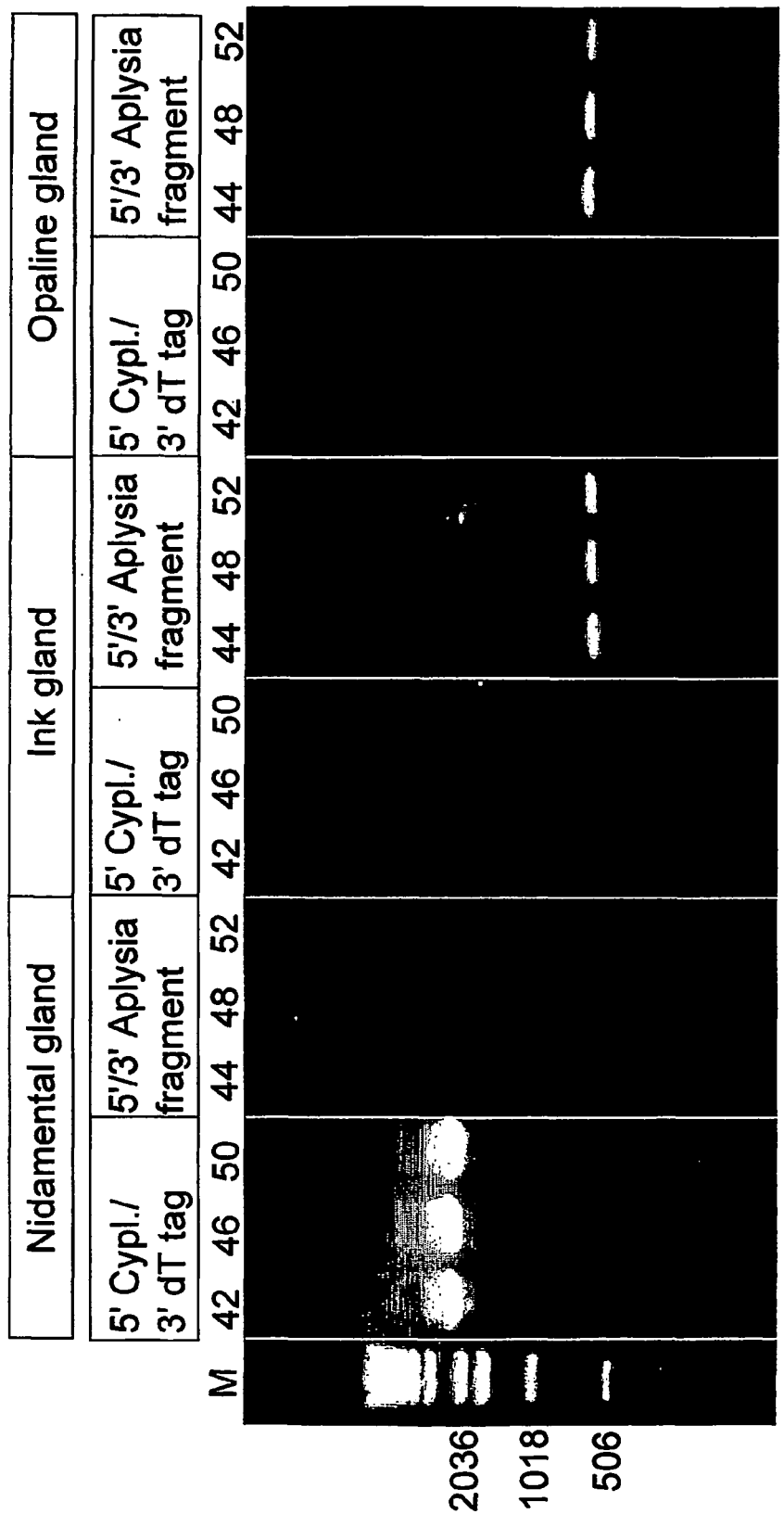

FIG. 19: Identification of a 2200 bp fragment of cyplasin L in the nidamental gland. M: markers for molecular weight. 42/46/48 or 44/48/52: annealing temperatures (° C.). 5' Cypl: 5' primer TC GCG GTC AGG TTC CTG GCG. 3' dT Tag: 3' primer (oligo dT-TCG ACG TTG TGT GGC TGC AT). 5'/3' *Aplysia* fragment: 5' primer CTG GGA ATT CCA GGA AAG CA, 3' primer TCG TGG CTG GAC ACC GAG AA.

Figure 20:
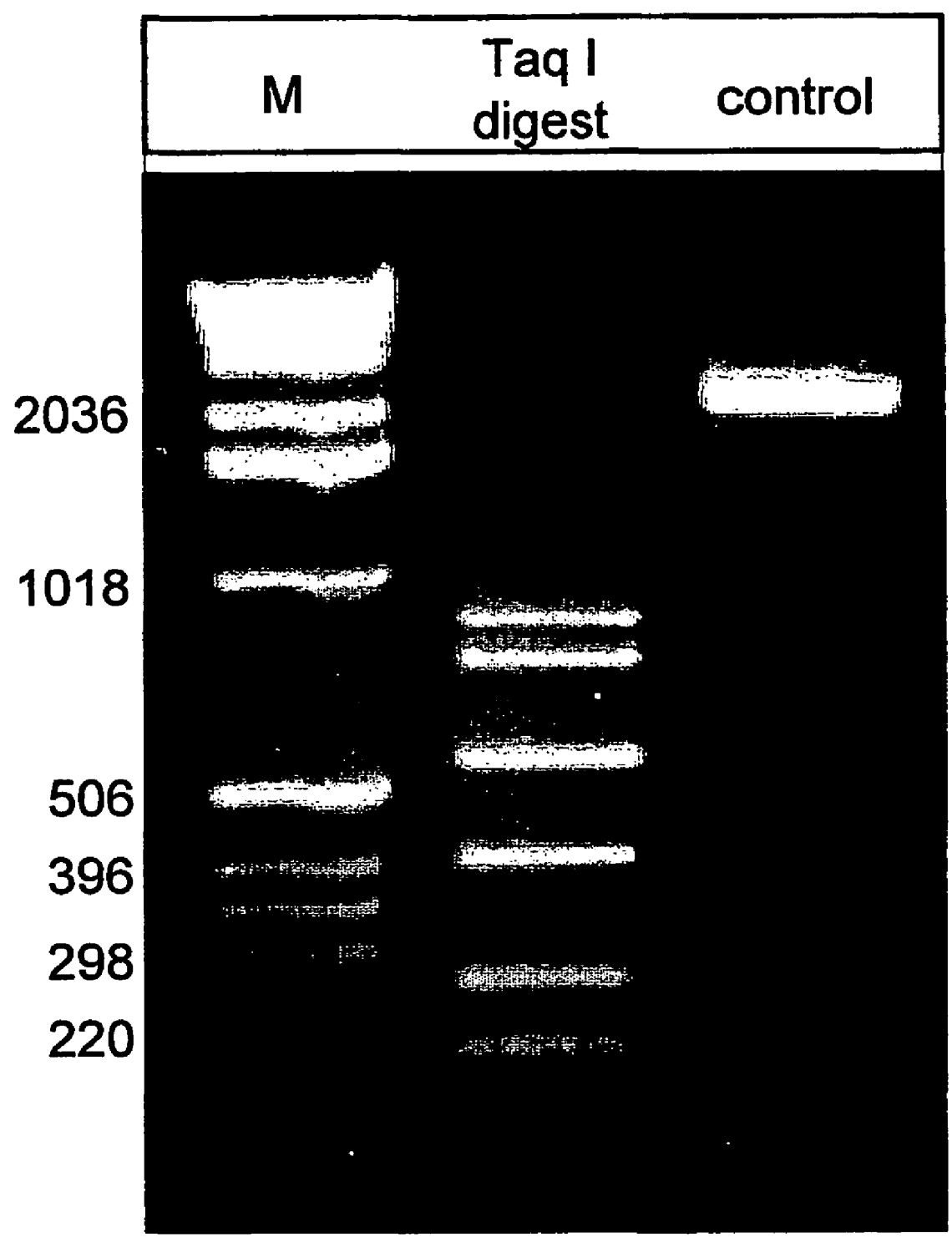

FIG. 20: Taq I digestion pattern of the 2200 bp fragment of cyplasin L. M: markers for molecular weight.

Figure 21:
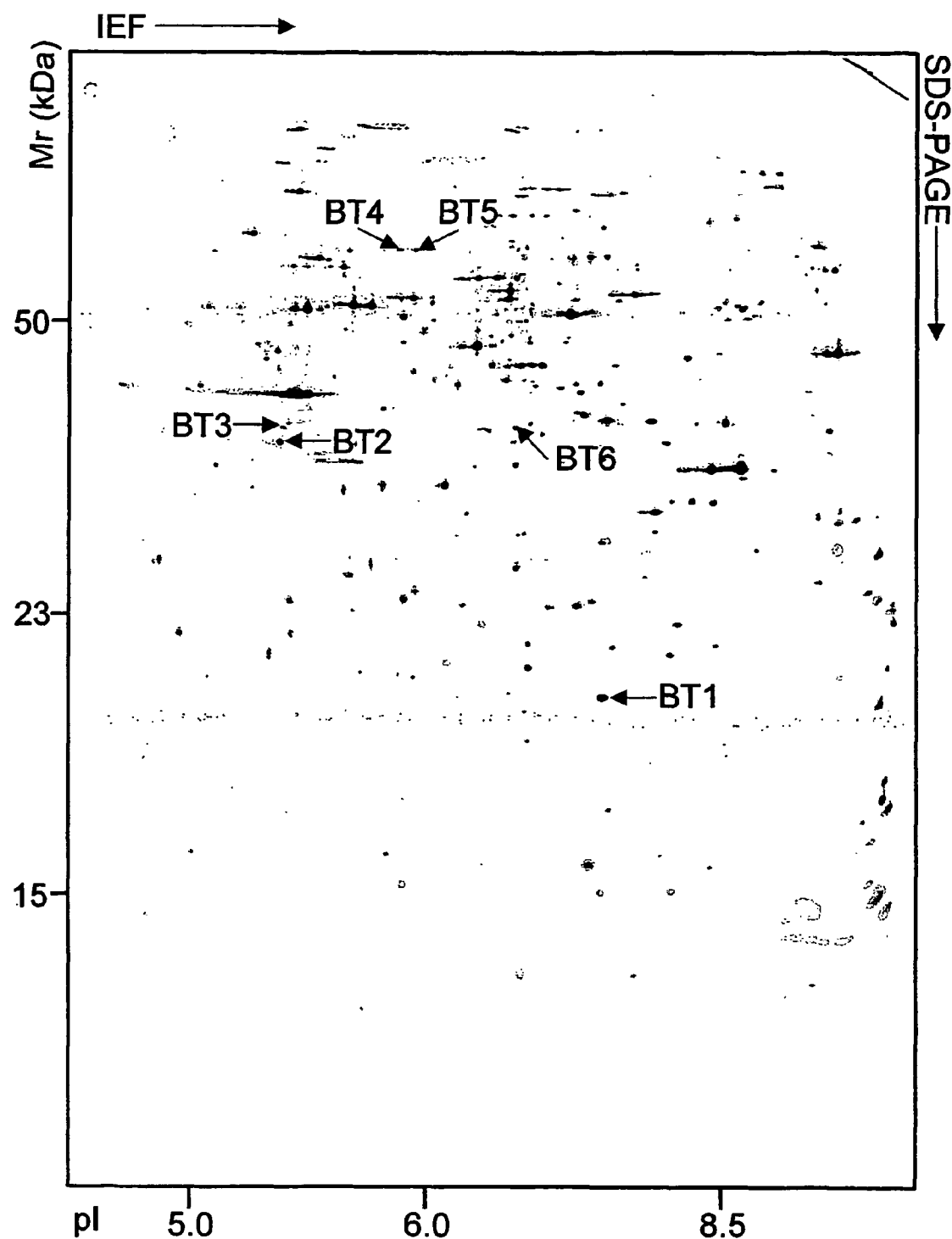

FIG. 21: 2-DE-gel of the membrane fraction of Jurkat T cells. The spots BT1 to BT6 were modified by treatment with *Aplysia punctata* ink.

Figure 22:
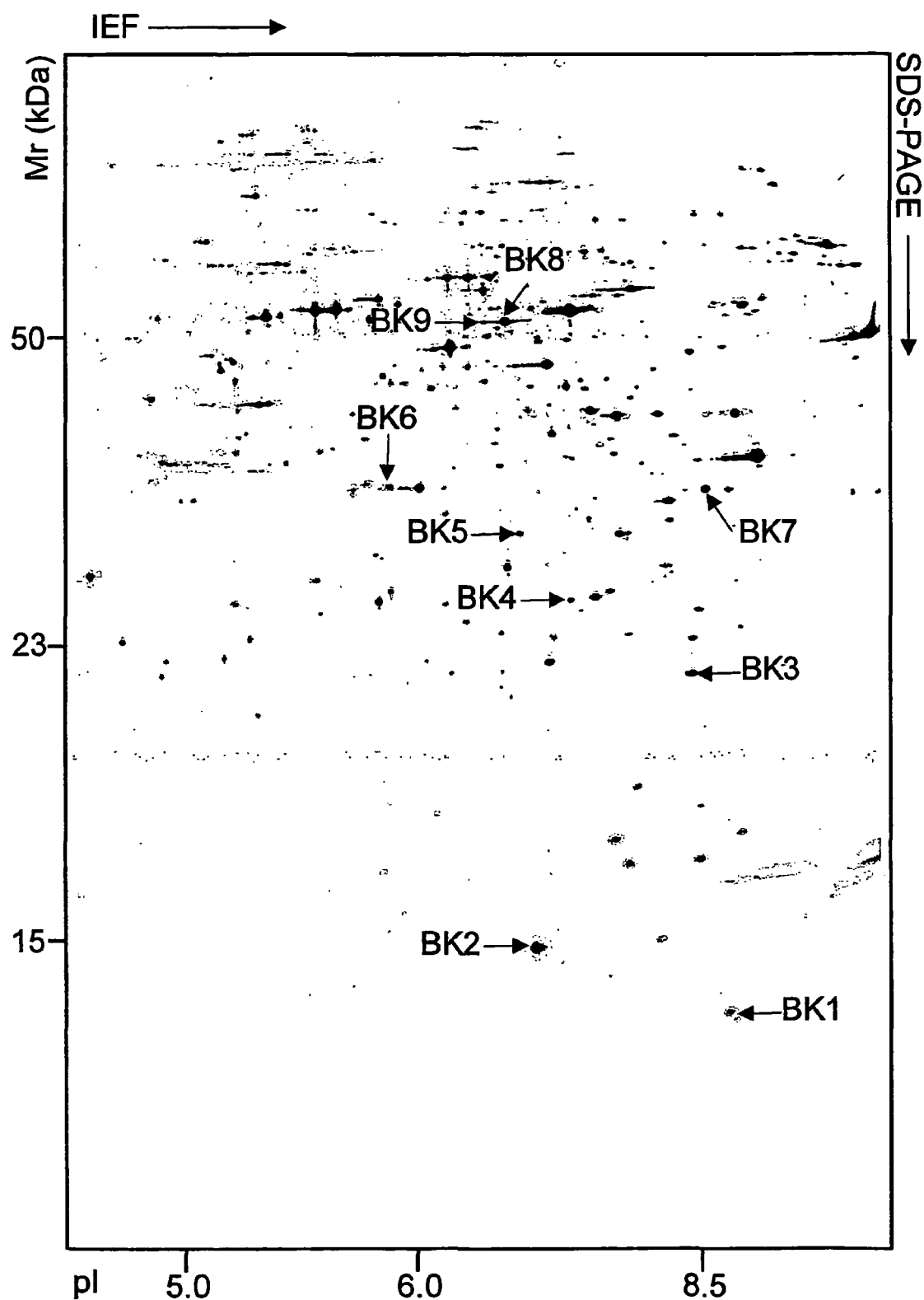

FIG. 22: 2-DE-gel of the membrane fraction of Jurkat T cells (control). The spots BK1 to BK9 were modified by treatment with *Aplysia punctata* ink.

Table 1:

Sensitivity of tumor cell lines to the cytotoxic *Aplysia* ink activity.

Table 2a:

Proteins modified by treatment with *Aplysia punctata* ink identified by 2-DE gel electophoresis, enzymatic digestion, and peptide mass fingerprinting.

The proteins were obtained from the total cell lysate. Name: internal name of the spots. Protein: common name of the protein. TopSpot is a public database at the Max Planck Institute for Infection Biology, Berlin, Germany (http://www.mpiib-berlin.mpg.de/2D-PAGE/) which describes identified and characterized proteins in total cell lysate of Jurkat T cells (Thiede et al. Electrophoresis 2000 July; 21(13):2713–20). The TopSpot numbers denote the spots on the 2-DE gels. Swiss-Prot, NCBI, Mw, and pI have their common meanings. Masses match describe the number of fragments obtained by MALDI-MS matching the predicted masses of the database protein. The sequence coverage describes the fraction of amino acid residues of the matching fragments relative to the number of amino acid residues of the database sequences. The motif describes import features of the sequence. The column $H_2O_2$ denotes those proteins modified by treatment with 500 µM $H_2O_2$ (yes) or not (no) or not determined (n.d.).

Table 2b:

Patterns of masses of the fragments of the proteins of Table 2a obtained by enzymatic digestion and peptide mass fingerprinting.

Table 3a:

Proteins of the membrane fraction modified by treatment with *Aplysia punctata* ink. For details, see legend of Table 2a.

Table 3b:

Patterns of masses of the fragments of the proteins of Table 3a obtained by enzymatic digestion and peptide mass fingerprinting.

Table 4:

Effect of NADPH oxidase inhibitor diphenylene iodonium (DPI) upon cell death induced by the cytotoxic activity obtained from *A. punctata* ink.

EXAMPLES

Example 1

Purification and Characterization of a Cytotoxic Activity from *Aplysia punctata* Ink 1. Methods 1.1 Purification of the Cytotoxic Activity from the Ink of *Aplysia punctata*

The ink was harvested by injecting 380 mM $MgCl_2$ into the body cavity and smooth massage of the sea hares. The ink was applied to a gel filtration Superdex HR200 column which was previously equilibrated with PBS. All fractions were analysed for their cytotoxic activity and the active fractions were pooled. The buffer of the pooled active fractions from the gel filtration were adjusted to 20 mM Tris, pH 8 (Centricon 10) and the samples were then applied to a MonoQ anion exchange column. Bound proteins were eluted using a linear NaCl gradient from 0–1000 mM NaCl.

1.2 One Dimensional Gel Electrophoresis

The SDS-PAGE system of Laemmli was used with 10% acrylamide. Electrophoresis was performed using a four-step increase of voltage, starting with 5 minutes at 35 V, followed by 10 minutes at 55 V, than 15 minutes at 100 V and finally 1 hour at 150 V.

1.3 Blotting on a Polyvinylidene Difluoride (PVDF) Membrane

Semi-dry blotting was performed with a TE 77 large semiphor transphor chamber (Pharmacia, Uppsala, Sweden) by using Immobilon-P PVDF membranes (Millipore, Eschborn, Germany). A current of 55 mA was applied for 2 hours.

1.4 Two Dimensional Gel Electrophoresis

The proteins were separated by a small gel 2-DE technique (gel size 8 cm×7 cm) by using a Protean Mini II chamber (Bio-Rad, Munich, Germany). The isoelectric focusing rod gels (1.5 mm diameter for preparative gels, 0.9 mm for analytical gels) contained 3.5% acrylamide, 0.3% piperazine diacrylamide (Bio-Rad, Munich, Germany) and a total of 4% w/v carrier ampholytes WITAlytes pH 2–11 (WITA GmbH, Teltow, Germany) and the protein was applied. After focusing, the gels were equilibrated for 10 minutes in a buffer containing 125 mM Tris/phosphate, pH 6.8, 40% glycerol, 70 mM DTT, and 3% SDS. The equilibrated gels were frozen at −70° C. After thawing, the isoelectric focusing gels were immediately applied to SDS-PAGE gels, which contained 15% w/v acrylamide and 0.2% bisacrylamide. The SDS-PAGE system of Laemmi was used, replacing the stacking gel by the equilibrated IEF gel. Electrophoresis was performed using a four-step increase of voltage, starting with 5 minutes at 35 V, followed by 10 minutes at 55 V, than 15 minutes at 100 V and finally 1 hour at 150 V.

1.5 Staining of the Gels with Coomassie Blue R-250

Preparative gels were stained with Coomassie Brilliant Blue R-250 (Serva, Heidelberg, Germany). After fixation over night in 1 l 50% ethanol/10% acetic acid/40% water, the gel was stained for at least 5 hours in 1 l 50% methanol/10% acetic acid/40% water, 1 g Coomassie Blue R-250. The staining solution was removed and the gel was washed for 1 hour with 1 l 5% methanol/12.5% acetic acid/82.5% water. Subsequently, the gel was kept for 4 hours in aqueous 7% acetic acid and can be stored at 4° C. in a plastic foil.

1.6 Staining of the PVDF Blot with Coomassie Blue R-250

PVDF membranes were stained with Coomassie Brilliant Blue R-250 (Serva, Heidelberg, Germany). The membrane was shaken in the staining solution (40% ml methanol/10% acetic acid/40% water, 0.1% Serva Blue R-250) for five minutes. Subsequently, the membrane was shaken three times for 5 minutes in the destaining solution (40% methanol/10% acetic acid) and finally dried.

1.7 Staining of the Gels with Silver Nitrate

Analytical gels were stained with silver nitrate. After fixation for at least one hour in 1 l 50% ethanol/10% acetic acid/40% water, the gel was incubated for 2 hours in 1 l 30% ethanol/0.5 M sodium acetate/0.5 glutaraledehyde/0.2% sodium thiosulfate. After washing with water for twice for 20 minutes, the gel was stained with 1 l 0.1% silver nitrate/0.01% formaldehyde for 30 minutes. After washing for 30 seconds, the gel was developed for at least 4 minutes in 2.5% sodium carbonate, pH 11.3/0.05 mM sodium thiosulfate/0.01% formaldehyde. The staining process was stopped by applying 0.05 M Titriplex III/0.02% Thimerosal. The solution was renewed after 15 minutes. Finally, the gels were dried for 3 hours at 70° C. between cellophane membranes using a gel dryer.

1.8 Tryptic Digestion

The Coomassie Blue R-250 stained single gel spots were excised with a scalpel. Equilibration of the gel pieces was performed by addition of 70 µl 50 mM ammonium bicarbonate, pH 7.8 for 30 minutes at 37° C. under shaking. Subsequently, shrinkage of the gel spots was performed by addition of 105 µl acetonitrile and shaking for 30 minutes at 37° C. After removing of the solution first equilibration, then shrinkage and finally equilibration were performed again. Then the gel spots were dried in a Speed Vac Concentrator (Eppendorf, Hamburg, Germany) after removing the equilibration solution. Next, 0.1 µg of trypsin (Promega, Madison, Wis., USA) solved in 1 µl 50 mM acetic acid and 19 µl 50 mM ammonium bicarbonate, pH 7.8 was added. After incubation at 37° C. for 16 hours the supernatant was removed and the gel pieces were washed with 20 µl 0.5% aqueous TFA/acetonitrile (1:1) and again the supernatant was removed. The combined supernatants were evaporated in the Speed Vac Concentrator and solved in 2 µl 0.5% aqueous TFA/acetonitrile (2:1) for the mass spectrometrical analysis.

1.9 Peptid Mass Fingerprinting by MALDI-MS

The mass spectra were recorded by using a time-of-flight delayed extraction MALDI mass spectrometer (Voyager-Elite, Perseptive Biosystems, Framingham, Mass., USA). The samples were mixed in an Eppendorf tube with the same volume of the matrix solution. Twenty mg/ml α-cyano-4-hydroxycinnamic acid in 0.3% aqueous TFA/acetonitrile (1:1) or 50 mg/ml 2,5-dihydroxybenzoic acid in 0.3% aqueous TFA/acetonitrile (2:1) were used as matrices. The mixtures in a volume of 0.6 µl were applied to a gold-plated sample holder and introduced into the mass spectrometer after drying. The spectra were obtained in the reflectron mode by summing 100–200 laser shots with the acceleration voltage of 20 kV, 70% grid voltage, 0.05 guide wire voltage, 100 ns delay and the low mass gate at 500 m/z.

1.10 Sequencing by ESI-MS/MS

The mass spectra were acquired with a quadrupole/time-of-flight ESI mass spectrometer equipped with a nebulized nanoelectrospray Z-spray source (Q-Tof, Micromass, Manchester, GB). Therefore, the tryptic digest was purified with a ZipTip C-18 tip (Millipore, Eschborn, Germany). The sample was evaporated and then dissolved in 2 µl 1% acetic acid/49% water/50% methanol. Subsequently, 1 µl was introduced in the mass spectrometer using a nanospray needle to generate the mass spectra.

1.11 N-terminal Sequencing

The blotted protein was excised from the PVDF membrane and analysed with a Procise sequencer (Applied Biosystems, Weiterstadt, Germany).

1.12 Database Searches

The tryptic peptide masses were introduced in an protein identification program by using the peptide mass fingerprinting analysis software MS-Fit. The databases NCBI and SwissProt with all species were used for the searches by considering a mass accuracy of 100 ppm, at maximum two missed cleavage sites, pyro-Glu formation at N-terminal Gln, oxidation of methionine, acetylation of the N-terminus and modification of cysteines by acrylamide.

A BLAST search against nr and a FASTA search against SWALL was performed for the analysis of the N-terminal and internal sequences.

2. Results

2.1 Cytotoxic Activity of A. punctata Ink

We harvested the ink from 4 sea hares and tested their cytotoxic activity towards Jurkat T cell line E6 (ATCC TIB 152). 1 µl of the crude ink containing about 5 µg protein was added to $4.2 \times 10^5$ Jurkat T cells in 1 ml RPMI medium. Within 6 h after challenge the cells lost their cell to cell contact and the nuclei started to shrink. After 12 h the nuclei of all the cells had shrunken to about half of the size of the buffer treated control. Although nuclear condensation is typical for an apoptotic cell death the mode of cell death induced by A. punctata ink is different from apoptosis since i) nuclei were not fragmented, ii) cells did not form apoptotic bodies and iii) DNA was not fragmented as measured by DNA ladder analysis. The mode of cell death elicited by the ink of A. punctata is also not typical of necrosis which is characterised by swollen cells and nuclei.

2.2 Purification of the Cytotoxic Activity

In order to identify the toxic activity in A. punctata ink we first determined the nature of the activity. Heating of the ink to 65° C. for 10 min abolished the activity completely suggesting that the activity is a protein.

Digestion with different proteases (e.g. pronase, trypsin, or proteinase K) did not abolish the activity. Thus, the active protein fragment may be very small and/or may be protected by carbohydrate or lipid residues. Further, a factor of low molecular weight which might be bound to the polypeptide (either covalently or non-covalently) may be the active compound.

In order to identify the active protein we separated the crude extract by gel filtration and tested the fractions for activity. The pooled fractions contained proteins of the approximate molecular masses of APL1, 2, 3 and 4 (62, 60, 58 and 57 kDA) but none of the other proteins present in the crude ink (FIG. 1). The pooled fractions were further separated over anion exchange chromatography which yielded only one active fraction (fraction 15). Analysis of the active fraction 15 by SDS-PAGE and silver staining showed that protein APL-3 was present while APL-3 was missing in the inactive fraction 14 and 16. Thus protein APL-3 exhibits the cytotoxic activity towards leukaemia T cells.

2.3 Identification of Proteins APL-1, -2, -3 and -4

The proteins APL-1–APL-4 were analysed by peptide mass fingerprinting (for APL-1 see FIG. 2; for APL-3 see FIG. 3). The same mass spectra were obtained for APL-2, -3 and -4 whereas a different mass spectrum was obtained for APL-1. This shows that proteins APL-2 to -4 exhibit the identical primary amino acid sequence while APL-1 does not share homology to APL-2 to -4. ESI-MS/MS and N-terminal sequence analysis was performed for APL-3. The putative sequence D-G-E-D-A-A-V was obtained by ESI-MS/MS of the tryptic peptide fragment with the mono protonated mass 1543.8 Da (FIG. 4). The N-terminal sequence analysis revealed the sequence (DQ)-G-(IV)-C-R-N-(QR)-R-(QP), whereby two possible amino acids were found at position 1,3,7 and 9 which are displayed in parenthesis.

The protein APL-1 was analysed by ESI-MS/MS. The following three putative sequences were obtained by ESI-MS/MS: F-A-D-S of the tryptic peptide fragment with the mono protonated mass 1137.8 Da (FIG. 5), G-P-D-G-(IL)-V-A-D of the tryptic peptide fragment with the mono protonated mass 1766.6 Da (FIG. 6) and P-G-E-V-S-(KQ)-(IL) of the tryptic peptide fragment with the mono protonated mass 1921.5 Da (FIG. 7).

2.4 Database Searches

The database searches using the masses and sequences of APL-1, -2, -3 and -4 with MS-Fit, BLAST and FASTA revealed no conformity with a known protein.

Example 2

Sensitivity of Tumor Cell Lines to the Cytotoxic Activity Obtained from *Aplysia* Ink Cells were incubated for 14 h in the presence of purified *Aplysia* cytotoxic activity (obtained from *Aplysia punctata* ink via gel filtration and anion exchange chromatography). The number of dead cells was determined by FACS analysis after staining with propidium iodide (PI).

In another protocol, the activity of lactate dehydrogenase (LDH), which is released by dead cells was determined from the culture supernatants (Cytotoxicity Detection Kit—LDH, Roche 1644793). The fraction of lysed cells was determined as the ratio of LDH activity from ink treated cells relative to LDH activity of Triton X100 lysed cells.

In a first experiment the sensitivity of Jurkat neo cells was compared with the sensitivity of PBMCs from healthy donors (dose response curves in FIGS. 12 and 13). The same results were obtained with the PI and the LDH protocol. At maximal response, about 80% of Jurkat neo cells, but only 28% of PBMCs were lysed (control level 2% and 1%, respectively). Thus, about 70% of the PBMCs are completely insensitive to the cytotoxic activity, whereas the fraction of insensitive Jurkat neo cells was only 20%. It is concluded that healthy cells are much more resistant to the *Aplysia* cytotoxic activity than tumor cells.

In a second experiment, the sensitivity of different tumor cell lines to the cytotoxic activity was determined (only LDH protocol). The $IC_{50}$ describes the concentrations of the cytotoxic activity at which half of the maximal response is reached. The following cell lines have $IC_{50}$ smaller than 10 pM (calculated with a molecular weight of 60 kDal): MCF-7neo/MCF-7-Bcl-$x_L$ (breast adenocarcinoma), SKW-Neo/SKW-Bcl-2 (acute myeloid leukemia, AML), GLC4/GLC4-ADR (MDR tumor cells, obtained by selection with adriamycin; small cell lung cancer).

From the fact that Jurkat Bcl-2, CEM Bcl-$x_L$, and K562 cells (resistant against apoptosis induction) are sensitive to the cytotoxic activity we conclude that the mechanism of cell death of the cytotoxic acitivty must be different from apoptosis.

Example 3

Different Protein Expression Pattern in Jurkat T Cells after Treatment with *A. punctata* Ink Methods Cell Culture The Jurkat T cell line E6 was maintained in RPMI tissue culture medium (Gibco BRL, Karlsruhe, Germany) supplemented with 10% fetal calf serum (Gibco BRL, Karlsruhe, Germany) and penicillin (100 U/ml)/streptomycin (100 µg/ml) (Gibco BRL, Karlsruhe, Germany) at 37° C. in 5.0% $CO_2$.

Treatment with *Aplysia punctata* Ink

Jurkat T cells ($5 \times 10^5$/ml) were incubated with ink from *A. punctata* (final dilution 1:500 or 1:1000) for 8 h at 37° C. in 5.0% $CO_2$ in the presence of 1 µg/ml cycloheximide. Controls were performed without ink.

Induction of Apoptosis

Apoptosis was induced to $2 \times 10^6$ Jurkat T cells for 6 h at 37° C. in 5.0% CO2 by 250 ng/ml αCD95 (clone CH11) (Immunotech, Marseille, France). 1 µg/ml cycloheximide was added to the control- and the Fas induced cells.

Total Cell Lysate

The Jurkat T cells were solubilized in 5 volumes of a buffer containing 9 M urea, 25 mM Tris/HCl, pH 7.1, 50 mM KCl, 3 mM EDTA, 70 mM DTT, 2.9 mM benzamidine, 2.1 µM leupeptin, 0.1 µM pepstatin, 1 mM PMSF, and 2% carrier ampholytes (Servalyte pH 2–4, Serva, Heidelberg, Germany). After 30 minutes of gentle stirring at room temperature, the samples were centrifuged at 100000 g (Ultracentrifuge Optima TLX, Beckman, München, Germany) for 30 minutes with a TLA120.2 rotor, which were kept at room temperature before centrifugation. The clear supernatant was frozen at −70° C.

Separation of the Compartments

Approximately $1 \times 10^8$ Jurkat T cells were centrifuged for 10 min at 1300 U/min at room temperature in a Megafuge 1.0R (Heraeus, Hanau, Germany). The supernatant was discarded and the pellet was washed twice with 10 ml PBS (GibcoBRL, Karlsruhe, Germany) and once with MB buffer (400 mM sucrose, 50 mM Tris, 1 mM EGTA, 5 mM 2-mercaptoethanol, 10 mM potassium hydrogenphosphate pH 7.6 and 0.2% BSA) and centrifuged as above. The pellet was suspended in MB buffer (4 ml/$10^8$ cells) and incubated on ice for 20 min. Subsequently the cells were homogenized and centrifuged at 3500 U/min for 1 min at 4° C. (Rotor SS-34; Sorvall RC5B, Hanau, Germany). The supernatant contained the mitochondria/cytosol/membranes and the pellet enclosed the nucleus.

The mitochondrial fraction was pelleted by centrifugation at 8600 U/min for 10 min at 4° C. (Rotor SS-34; Sorvall RC5B, Hanau, Germany). The supernatant contained the cytosol and membranes.

The pellet was suspended in MSM buffer (10 mM potassium hydrogenphosphate pH 7.2, 0.3 mM mannitol and 0.1% BSA) (0.4 ml/$10^8$ cells) and purified by sucrose gradient centrifugation in 10 ml SA buffer (1.6 M sucrose, 10 mM potassium hydrogenphosphate pH 7.5 and 0.1% BSA) and 10 ml SB buffer (1.2 M sucrose, 10 mM potassium hydrogenphosphate pH 7.5 and 0.1% BSA) at 20000 U/min, 1 hour, 4° C. (Rotor SW-28; Beckman L8-70M Ultracentrifuge, München, Germany). The interphase which contained the mitochondria was collected, suspended in 4 volumes of MSM buffer and centrifuged again at 15500 U/min for 10 min. at 4° C. (Rotor SS-34; Sorvall RC5B, Hanau, Germany). The pellet was suspended in MSM buffer without BSA and could be stored at −70° C.

The supernatant with the cytosol and membrane was centrifuged at 100000 U/min, 20 min, 4° C. (Rotor TLA120.2 rotor, Ultracentrifuge Optima TLX, Beckman, München, Germany). The pellet contained the membranes.

The pellet with the nucleus was suspended in 5 ml PBS and centrifuged for 2 min at 3500 U/min at 4° C. (Rotor SS-34; Sorvall RC5B, Hanau, Germany). The pellet was suspended in NB buffer (10 mM Hepes pH 7.4, 10 mM KCl, 2 mM MgCl2, 1 mM DTT and 1 mM Pefabloc) (1 ml/$10^8$ cells) and incubated for 1 hour on ice, subsequently homogenized and applied to 10 ml 30% sucrose in NB buffer. After the centrifugation with the Megafuge 1.0R (Heraeus, Hanau, Germany) at 2000 U/min for 10 min at 4° C., the pellet was washed twice with 6 ml NB buffer, centrifuged as above, suspended in 1 ml NB buffer, and centrifuged again at 10000 U/min for 10 minutes at 4° C. (Rotor SS-34; Sorvall RC5B, Hanau, Germany). The pellet could be stored at −70° C.

2D Gel Electrophoresis

The proteins were separated by a large gel 2-DE technique (gel size 30 cm×23 cm). The isoelectric focusing rod gels (diameter 1.5 mm or 2.5 mm for preparative gels, 0.9 mm for analytical gels) contained 3.5% acrylamide, 0.3% piperazine diacrylamide (Bio-Rad, Munich, Germany) and a total of 4% w/v carrier ampholytes WITAlytes pH 2–11 (WITA GmbH, Teltow, Germany). About 25 μl for preparative gels containing about 200 μg of protein or 6 μl for analytical gels containing 50 μg of protein were applied to the anodic side of the gel and focused at 8870 Vh. After focusing, the gels were equilibrated for 10 minutes in a buffer containing 125 mM Tris/phosphate, pH 6.8, 40% glycerol, 70 mM DTT, and 3% SDS. The equilibrated gels were frozen at −70° C. After thawing, the isoelectric focusing gels were immediately applied to SDS-PAGE gels, which contained 15% w/v acrylamide and 0.2% bisacrylamide. The SDS-PAGE system of Laemmli was used, replacing the stacking gel by the equilibrated IEF gel. Electrophoresis was performed using a two-step increase of current, starting with 15 minutes at 120 mA for preparative gels or 65 mA for analytical gels, followed by a run of about 6 hours at 150 mA for preparative gels or 85 mA for analytical gels, until the front reached the end of the gel.

Staining with Coomassie Blue G-250

Preparative gels were stained with Coomassie Brilliant Blue G-250 (Bio-Rad, Munich, Germany). After fixation over night in 1 l 50% methanol/2% phosphoric acid, the gel was washed three times with water, then the gel was incubated for 1 hour in 1 l 34% methanol/2% phosphoric acid/17% ammonium sulfate. Subsequently, 0.66 g Coomassie Blue G-250 was added for staining and the gel was incubated for four days. The staining solution was removed and the gel was washed for 1 minute with 1 l 25% methanol and afterwards with water. Subsequently, the gel can be stored at 4° C. in a plastic foil.

Staining with Silver Nitrate

Analytical gels were stained with silver nitrate. After fixation for at least one hour in 1 l 50% ethanol/10% acetic acid/40% water, the gel was incubated for 2 hours in 1 l 30% ethanol/0.5 M sodium acetate/0.5 M glutaraldehyde/0.2% sodium thiosulfate. After washing with water for twice for 20 minutes, the gel was stained with 1 l 0.1% silver nitrate/0.01% formaldehyde for 30 minutes. After washing for 30 seconds, the gel was developed for at least 4 minutes in 2.5% sodium carbonate, pH 11.3/0.05 mM sodium thiosulfate/0.01% formaldehyde. The staining process was stopped by applying 0.05 M Titriplex III/0.02% Thimerosal. The solution was renewed after 15 minutes. Finally, the gels were dried for 3 hours at 70° C. between cellophane membranes using a gel dryer (Model 585, Bio-Rad, München, Germany).

Tryptic Digestion

The Coomassie Blue G-250 stained single gel spots were excised with a scalpel and shrunk by addition of 100 μl 50 mM ammonium bicarbonate, pH 7.8/acetonitrile (1:1) for 30 minutes at 37° C. under shaking. Subsequently the solution was exchanged against 100 μl 50 mM ammonium bicarbonate, pH 7.8 for reswelling of the gel piece for 30 minutes at 37° C. under shaking. The gel spots were dried in a Speed Vac Concentrator (Eppendorf, Hamburg, Germany) after removing the buffer. 0.1 μg of trypsin (Promega, Madison, Wis., USA) solved in 1 μl 50 mM acetic acid and 19 μl 50 mM ammonium bicarbonate, pH 7.8 were added. After incubation at 37° C. for 16 hours the supernatant was removed and the gel pieces were washed with 20 μl 0.5% aqueous TFA/acetonitrile (2:1) and again the supernatant was removed. The combined supernatants were evaporated in the Speed Vac Concentrator and solved in 4 μl 0.5% aqueous TFA/acetonitrile (2:1) for the mass spectrometrical analysis.

Peptide Mass Fingerprinting by MALDI-MS

The mass spectra were recorded by using a time-of-flight delayed extraction MALDI mass spectrometer (Voyager-Elite, Perspective Biosystems, Framingham, Mass., USA). The samples were mixed in an Eppendorf tube with the same volume of the matrix solution. Twenty mg/ml α-cyano-4-hydroxycinnamic acid (CHCA) in 0.3% aqueous TFA/acetonitrile (1:1) or 50 mg/ml 2,5-dihydroxybenzoic acid (DHB) in 0.3% aqueous TFA/acetonitrile (2:1) were used as matrices. 0.6 μl of the mixtures were applied to a gold-plated sample holder and introduced into the mass spectrometer after drying. The spectra were obtained in the reflectron mode by summing 100–200 laser shots with the acceleration voltage of 20 kV, 70% grid voltage, 0.05 guide wire voltage, 100 ns delay and the low mass gate at 500 m/z.

Identification of the Proteins

The proteins were identified by using the peptide mass fingerprinting analysis software MS-Fit or Profound. Searches were performed in the databases NCBInr and SwissProt. Only human sequences were considered. In addition, oxidation of methionine, modification of cysteines by acrylamide and at maximum one missed cleavage site was taken into account.

Results

Identification of Protein Spots Modified by Treatment with *A. punctata* Ink

Cell death was induced in Jurkat T-cells by treatment with *A. punctata* ink for 8 hours. 2-DE gels were produced after lysis of the cells and separation of the proteins. A representative analytical 2-DE gel of ink treated cells is shown in FIG. 14. A representative analytical control gel of untreated cells is shown in FIG. 15. Approximately 2000 spots were resolved and detected by silver staining. Four 2-DE gels of ink treated cells were compared with four control 2-DE gels. In ink treated Jurkat T cells, thirteen additional spots were found (T10 includes two spots). In untreated Jurkat T cells, six additional spots were observed. Preparative Coomassie stained 2-DE gels were used for the identification by mass spectrometry.

Identified Proteins in the Total Cell Lysate

Fourteen proteins (Table 2a and 2b) within nineteen spots were identified by peptide mass fingerprinting after in-gel digestion with trypsin, elution of the generated peptides and analysis by DE-MALDI-MS. One protein (thioredoxin peroxidase 2, NCBI 548453) displayed a pI shift (and was found at different spot positions in control and ink treated cells). 60S ribosomal protein P0 (4506667 or 12654583) displayed a pI and mass shift. The other proteins were identified at one condition only: Hsp-60 (14603309), stathmin (5031851), Rho GDI 2 (1707893), RNA binding regulatory subunit (12720028), hnRNP C1/C2 (4758544), proteasome subunit beta type 1 (130853), pre-mRNA cleavage factor Im (5901926), proteasome subunit alpha type 7 (12643540), U2 small nuclear ribonucleoprotein A' (134094), GAP SH3 binding protein (5031703), DNA replication licensing factor MCM4 (1705520), and thioredoxin peroxidase 1 (2507169). The protein of the spot 4_62, was not yet identified.

Identified Proteins in the Membrane Fraction

In addition to several proteins identified in the total cell lysate, seven new proteins were identified in the membrane fraction (Table 3a and 3b, FIGS. 21 and 22).

Comparison of the 2-DE-pattern of Aplysia Ink Treated Cells with Patterns of Apoptic Cells (Total Cell Lysate).

FIG. 16 shows the 2-DE-pattern of total cell lysate of Fas-induced apoptotic Jurkat T cells. FIG. 17 shows the corresponding control gel. The proteins indicated in the gels by the spots PF1 to PF10 and NF1 to NF6 were modified during apoptosis.

Fas and Aplysia punctata ink induce modification of different sets of proteins. This can be seen by comparison of the patterns of the modified spots in the in gels of the Fas induced cells (FIG. 16) and ink treated cells (FIG. 14). As expected from this observation, almost all spots disappearing after Fas induction indicated in the control gel (FIG. 17) can be found in the gel showing ink treated cells (FIG. 14) without modification (at the same position). Almost all spots disappearing after ink treatment indicated in FIG. 15 (control) can be found in the gel showing Fas induced cells (FIG. 16) without modification. This clearly demonstrates that the effect of Aplysia ink treatment is different from Fas induced apoptosis mechanism. Only a few proteins were modified both by ink and Fas induction (e.g. hRNP C1/C2, spot T5 in FIG. 14; PF1 in FIG. 16 and NF1 in FIG. 17; GAP SH3 binding protein, T10 in FIG. 14, PF10 in FIG. 16). However, the modification of GAP SH3 binding protein in apoptosis is cleavage by caspases, whereas the modification after ink incubation is a shift in pI.

Example 4

Reactive Oxygen Species are Involved in Cell Death Induced by the Cytotoxic Activity Obtained from Aplysia Ink It is demonstrated that the effect of the cytotoxic activity obtained from the ink of A. punctata upon Jurkat T cells is very similar to the effect of high concentrations of $H_2O_2$. The ink effect can be inhibited by preincubation with an antioxidant or a specific blocker of NADPH oxidase/nitric oxide synthase.

At high concentrations of $H_2O_2$, cells die in a non-apoptotic phenotype due to the blockage of caspases (Hampton and Orrenius, 1997, FEBS Letters 414:552–556).

We analysed the proteome of $H_2O_2$ treated Jurkat T cells. The experimental protocols are described in example 2, with the modification that incubation was performed in the presence of 500 μM $H_2O_2$ instead of Aplysia punctata ink. We found that protein modifications observed in the 2-DE pattern of total cell lysate were identical after $H_2O_2$ incubation and after Aplysia ink incubation. The proteins modified after $H_2O_2$ incubation are listed in Tables 2 and 3 (column $H_2O_2$, "yes"). Examples of modified proteins are shown in FIG. 18.

Thus, the Aplysia cytotoxic activity may activate intracellular pathways leading to $H_2O_2$ production in large amounts. Caspases may be blocked or by-passed by the cytotoxic activity. In order to test this hypothesis, in a second experiment, we tested the effect of lipoic acid, a metabolic antioxidant, upon the effect of the cytotoxic activity. Jurkat T cells were incubated for 18 h in RPMI (10% FCS, 1 U/ml penicillin, 1 μg/ml streptomycin) including 100 μM lipoic acid (Sigma). Cells were centrifuged (120 g, 8 min, RT) and resuspended in fresh RPMI at a concentration of $5 \times 10^5$/ml. Native ink was added to the cell suspension (final dilution 1:250). After 6 h of incubation cells were washed with PBS and stained with propidium iodide (PI, final concentration 0.25 μg/ml). About 25000 cells were analysed in a DAKO Galaxy flow cytometer. PI stained cells were counted using the partec FloMax software. Controls were performed in the presence of ink alone, lipoic acid alone and without additives. The fraction of PI stainable cells after ink incubation was reduced by 69% in the presence of lipoic acid (control level subtracted). Lipoic acid alone had no effect. We concluded that an oxidative process is involved in cell death induced by A. punctata ink.

Production of reactive oxygen species (ROS) is due to the activation of NADPH oxidase. This enzyme is found in a variety of cells including phagocytes and T cells. Activation of T cell NADPH oxidase by A. punctata ink was tested by treatment with the specific inhibitor diphenylene iodonium (DPI) before incubating them with ink.

Jurkat neo cells harvested in the log phase were adjusted to a concentration of $5 \times 10^5$/ml in RPMI medium (10% FCS, 1 U/ml penicillin, 1 μg/ml streptomycin) were treated with 100 μM DPI (stock solution in DMSO, final concentration of DMSO was 0.4%) for 10 min (37° C., 5% $CO_2$). Control cells were incubated with 0.4% DMSO alone. Cells were centrifuged (120 g, 8 min, RT), washed and resuspended in 1 ml of fresh medium. 1 μl of an active fraction (called AEX-21) obtained from Aplysia ink via gel filtration and anion exchange chromatography was added. After 7 h of incubation (37° C., 5% $CO_2$) cells were washed once with PBS and stained with PI for FACS analysis. The percentage of PI-stained cells was calculated (Table 4).

The amount of dead cells was reduced from 60% to 33% (control level subtracted) in DPI preincubated cells. DPI alone had no effect. The results of this experiments demonstrate that a DPI sensitive mechanism is involved in the cytotoxic effect of Aplysia ink. This mechanism may include NADPH oxidase activation and thus the production of $H_2O_2$, oxygen radicals and/or other ROS.

Example 5

The mRNA for Cyplasin L is Located in the Nidamental Gland

This example describes the distribution of the cyplasin mRNAs in different *Aplysia* tissues.

We prepared three different tissues of *Aplysia punctata* (nidamental gland, mantle comprising the ink gland, and opaline gland). Details of *Aplysia* anatomy can be found in Richard Fox, Invertebrate anatomy (1994). The nidamental gland is a compound structure of the reproductive system. It contains the winding gland, mucus gland, albumen gland and fertilization chamber.

The total RNA of the three tissues was extracted using the Quiagen RNeasy mini kit (Quiagen, Hilden, Germany). Aliquots were transformed to cDNA by incubation for 50 min at 42° C. with reverse transcriptase (Superscript II, Life technologies, Karlsruhe, Germany) and an oligo-dT$_{18}$, which carries a short stretch of sequence (CGA ACT A TCGACGTTGTGTGGCTGCAT TAC, SEQ ID NO.15) for further PCR at the 3' region. Subsequently PCR was performed at different annealing temperatures (42, 46, 50° C.) applying primers for the 5' region of cyplasin (TC GCG GTC AGG TTC CTG GCG, SEQ ID NO.16) and the 3' sequence (oligo dT-TCG ACG TTG TGT GGC TGC AT, SEQ ID NO.17). An already cloned short sequence (~550 bp) derived from the mantle tissue/ink gland served as internal control (*Aplysia* fragment 5': CTG GGA ATT CCA GGA AAG CA, SEQ ID NO.18; 3': TCG TGG CTG GAC ACC GAG AA, SEQ ID NO.19; annealing temperatures 44, 48, 52° C.).

With the 5' cyplasin primer we obtained a specific product (~2200 bp) in a cDNA pool derived from the nidamental gland, but not in cDNA derived from the ink gland and from the opaline gland. The 550 bp control fragment was obtained from cDNA derived from all three tissues (FIG. 19).

A restriction digest of the 2200 bp PCR product obtained with the cyplasin-5'-primer using Taq I (NEB, Frankfurt am Main, Germany) renders a pattern of fragments (~900 bp, ~800 bp, ~550 bp, ~400 bp, ~260 bp, ~200 bp, FIG. 20) which is identical to the theoretical cyplasin L pattern (49 bp, 197 bp, 263 bp, 405 bp, 561 bp and 526 bp) obtained from virtuell cleaving the nucleotide sequence of cyplasin L (11967690) with the clone manager 5 software (Scientific & Educational Software). The 526 bp-fragment, which comprises parts of the poly-A tail, may be of variable length due to random binding sites of the oligo-dt$_{18}$ primer. This may account for at least one of the two largest additional fragments (~800 bp). The pattern obtained by virtuell cleavage of cyplasin S (fragments of 443 bp, 405 bp, 329 bp, 312 bp, and 197 bp) does not fit to the experimental pattern.

We conclude that cyplasin L is produced in the nidamental gland but neither in the ink gland (including the mantle region) nor in the opaline gland of *Aplysia punctata*.

Example 6

Partial Sequence of a Nucleic Acid Encoding a Polypeptide Having Cytotoxic Activity Total RNA of *Aplysia punctata* nidamental and albumen gland was isolated as described in Example 5. The RNA was used to reverse transcribe RNA to cDNA by the use of a polyT oligonucleotide (CGA ACT ATC GAC GTT GTG TGG CTG CAT TAC TTT TTT TTT TTT TTT TTT, SEQ ID NO.20). The cDNA was used as template in a PCR reaction with a degenerated oligonucleotide TC GGT MAR GAC GGI GAA GAC (SEQ ID NO.21) deduced from the partial amino acid sequence K/Q D G E D of the polypeptide having cytotoxic activity and a second primer directed against the poly-T-TCG ACG TTG TGT GGC TGC AT (SEQ ID NO.17). The resulting fragment was cloned and the DNA sequence of the fragment was deduced from both sites.

The partial sequences of the nucleic acid encoding a polypeptide having cytotoxic activity is (N: A, T, C or G; underlined is the sequence of the oligonucleotide):

5':
CAAGACGGGGAAGACAAGGAGTTTGACGGAGAAATCGTCAGCGTCAGAGT

GCTGAAGGCGTTCGGCAAGCCTGGCTACGGTTACAAGCAGCCCTCGTGCA

AGGAAGGCAAGGACTACGTGAGCAGCGGCAGCGTTCTTCACGTGCTGCAG

TGTGCCGGCTTCTTCGAGGTGTGCTACGAGAGAGGATCACCACCCAGCCA

GCCACGACTGTCGCTGCAGCAGAGGTACAATGCAAAAAGTTCATCGCAAC

CCACAAATTGGAGGAGACTGTTGATGGAAGGATCGTCAGCATCGAGCTTG

TCCAGAGACTGAAGAAACAATCCGGATACGGTCCAAGTGGCGGTTCTGGT

TATGGCAACGGTCATGGTCAAAGACCCGGTTACGGATACGGTTCTGGTAG

TGGAAGTGGCTACGCCCCCAGAGGAGGATACAACCCAAAAG

3':
TACCGCCCCCGCCACCACTNTNGCACCAGCAGAACCAACCTGCGAGAAGC

TGTCCGTNTGGTTCAACGTGGANAGATTCGAAGGTTCCAGATCGTGAGTT

TCAAGCTCATCCGCCTGTTCAACAGGTNCAAGAAGTGCAAGAAAGNCCAG

TATTCCGTGTCTGGCGATGATGAGGACNCATTCGTTGTCAGTGGTTGTTC

TGGCGTGTTCCAGGTNTGCTACGAAGAACAACGGCGCCCGCTACAACCNC

CACAGAAGCCCCGAAGCCAGAGCCAAGAAGACCCAAGAGGAAAAATTTCC

CAATCAAATTTNGTAAACACTGATGGGTTAATNTGACGACCAGTGCGTCT

GCGAAAGAATCATGTTATGGTTCATGATGTCATGCTCTTAATATAGGTTG

TAACGTTTAACGCGATACAGACATTAAAACTCATTGTTCAAAAAAAAAAA

AAAAAAA

The nucleotide sequences are identified as SEQ ID NOs.9 and 11.

The translated amino acid sequence of the 5' sequence (SEQ ID NO.10) is:

QDGEDKEFDGEIVSVRVLKAFGKPGYGYKQPSCKEGKDYVSSGSVLHVLQ

CAGFFEVCYEERITTQPATTVAAAEVQCKKFIATHKLEETVDGRIVSIEL

VQRLKKQSGYGPSGGSGYGNGHGQRPGYGYGSGSGSGYAPRGGYNPK

The translated amino acid sequences (three possible reading frames) of the 3' sequence (SEQ ID NOs. 12, 13 and 14 (?: amino acid cannot be determined; *: STOP codon)

1:
YRPRHH??TSRTNLREAVR?VQRG?EIRRFQNREFQAHPPVQQ?QEVQE?

PVFRVWR**G?IRCQWLFWRVPG?LRRTNGARYN?HRSPEARAKKTQEEK

FPNQI?*TLMG*?DDQCVCERIMLWFMMSCS*YRL*RLTRYRH*NSLFKK

KKKK

2:
TAPATT?APAEPTCEKLS?WFNV?KKFEGSRIVSFKLIRLFNR?KKCKK?

-continued

QYSVSGDDED?FVVSGCSGVFQ?CYEEQTAPATT?TEAPKPEPRRPKRKN

FPIKF?KH*WVN?TTSASAKESCYGS*CHALNIGCNV*RDTDIKTHCSKK

KKK

3:
PPPPP??HQQNQPARSCP?GSTW?RNSKVPES*VSSSSACSTG?RSARK?

SIPCLAMMR?HSLSVVVLACSR?ATKNKRRLQ?PQKPRSQSQEDPRGKIS

QSN?VNTDGL?*RPVRLRKNHVMVHDVMLLI*VVTFNAIQTLKLIVQKKK

KK

Example 7

NANA Does Not Influence the Cytotoxic Activity of *A. punctata* Ink

The cytotoxicity of Aplysianin P has been shown to be completely inhibitable by N-acetylneuraminic acid (NANA) in a concentration of 50 mM (Yamazaki M., 1989, Cancer Research 49, 3834–3838). Here, the effect of 50 mM NANA on the cytotoxic activity of native *A. punctata* ink was tested.

Jurkat neo cells were harvested in the log-phase and centrifuged as usual (see example 4 for details). The cells were adjusted to a concentration of $5 \times 10^5$/ml with fresh RPMI (10% FCS, 1 U/ml penicillin, 1 µg/ml streptomycin) including 50 mM NANA (SIGMA). Because of the acidity of NANA ~35 mM NaOH was added to the medium (prior to resuspending cells) to reach a final pH of about 7.4.

After one hour of preincubation at 37° C. and 5% $CO_2$ native ink was added to the cell suspension (final dilution 1:200). After 7 h of further incubation cells were washed once with PBS and stained and analysed as described in example 4.

FACS analysis showed no difference in mortality between cells incubated with NANA and ink (62% PI stained cells) and cells treated with ink alone (50%). Cells without any treatment and cells treated with NANA alone showed 6% and 7% PI staining, respectively.

We therefore conclude that the presence of N-acetyl-neuraminic acid does not affect the cytotoxic activity of *A. punctata* ink.

TABLE 1

| Tumor cell line | ATCC number | Type | Features | $IC_{50}$ |
|---|---|---|---|---|
| Jurkat neo | | acute lymphoid leukemia T cells | | 2.4 pM |
| Jurkat Bcl-2 | | acute lymphoid leukemia T cells | Bcl-2 overexpression, resistant to apoptosis | 1.6 pM |
| CEM Neo | | acute lymphoblastic leukemia | | 24 pM |
| CEM Bcl-$x_L$ | | acute lymphoblastic leukemia | Bcl-$x_L$ overexpression, resistant to apoptosis | 8 pM |
| K562 | CCL-243 | chronic myeloid leukemia | resistant to apoptosis | 11.2 pM |

TABLE 2a

| Name | Protein | Top Spot | Swiss-Prot | NCBI | Mw | Mw found | pI | pI found | Masses match | Sequence Coverage | Motif | $H_2O_2$ |
|---|---|---|---|---|---|---|---|---|---|---|---|---|
| K1 | Thioredoxin peroxidase 2 | 4_504 | Q06830 | 548453 | 22.09 | 22.10 | 8.7 | 8.3 | 17 | 75% | AhpC/TSA family | yes |
| K2 | 60S ribosomal protein P0 | 3_300 | | 12654583 | 34.26 | 33.50 | 5.4 | 5.8 | 10 | 33% | | yes |
| K3 | | 4_62 | | | | 18.00 | | 6.2 | | | | yes |
| K4 | Hsp-60 (N-term) | 1_372 | | 14603309 | 59.79 | 45.90 | 5.5 | 6.0 | 17 | 40% | | yes |
| K5 | Stathmin | 5_6 | | 5031851 | 17.28 | 17.50 | 5.8 | 5.6 | 11 | 48% | | yes |
| K6 | Rho GDI 2 | 3_192 | P52566 | 1707893 | 22.97 | 23.00 | 5.1 | 5.2 | 12 | 64% | | yes |
| T1 | Thioredoxin peroxidase 2 | | Q06830 | 548453 | 22.09 | 22.10 | 8.7 | 8.0 | 17 | 79% | AhpC/TSA family | yes |
| T2 | 60S ribosomal protein P0 | | | 4506667 | 34.26 | 32.80 | 5.7 | 6.1 | 13 | 55% | | yes |
| T3 | RNA binding regulatory subunit | | O14805 | 12720028 | 19.87 | 22.10 | 6.3 | 5.8 | 13 | 57% | ThiJ/Pfpl family | yes |
| T4 | hnRNP C1/C2 | | | 4758544 | 31.95 | 36.30 | 5.1 | 5.1 | 10 | 27% | | yes |
| T5 | hnRNP C1/C2 | | | 4758544 | 31.95 | 37.10 | 5.1 | 5.1 | 7 | 20% | | yes |
| T6 | Proteasome subunit beta type 1 | | P20618 | 130853 | 26.47 | 24.30 | 8.7 | 8.3 | 10 | 40% | Proteasome | yes |
| T7 | Pre-mRNA cleavage factor lm | 4_325 | | 5901926 | 26.21 | 25.50 | 8.9 | 8.5 | 12 | 34% | — | yes |
| T8 | Proteasome subunit alpha type 7 | | O14818 | 12643540 | 27.87 | 27.90 | 8.8 | 8.3 | 7 | 40% | Proteasome | yes |
| T9 | U2 small nuclear ribonucleo-protein A | | P09661 | 134094 | 28.43 | 29.90 | 8.9 | 8.5 | 15 | 53% | Leucine Rich Repeat | yes |
| T10 | GAP SH3 binding protein | | | 5031703 | 52.20 | 69.20 | 5.4 | 5.8 | 13 | 36% | | yes |

TABLE 2a-continued

| Name | Protein | Top Spot | Swiss-Prot | NCBI | Mw | Mw found | pI | pI found | Masses match | Sequence Coverage | Motif | $H_2O_2$ |
|---|---|---|---|---|---|---|---|---|---|---|---|---|
| T11 | DNA replication licensing factor MCM4 | | P33991 | 1705520 | 96.61 | 85.00 | 6.3 | 6.7 | 19 | 27% | MCM | yes |
| T12 | Thioredoxin peroxidase 1 | 3_255 | P32119 | 2507169 | 21.87 | 21.00 | 5.7 | 5.6 | 10 | 42% | AhpC/TSA family | yes |

TABLE 2b

| Name | Protein | Masses of Fragments (Dal) |
|---|---|---|
| K1 | Thioredoxin peroxidase 2 | 819.42, 888.44, 894.44, 920.51, 980.53, 1107.60, 1164.56, 1196.63, 1211.68, 1359.81, 1475.78, 1622.87, 1750.93, 1778.96, 1794.95, 1907.04, 2420.18, 2781.29 |
| K2 | 60S ribosomal protein P0 | 720.39, 748.48, 771.38, 803.43, 819.41, 874.47, 875.45, 968.50, 1033.59, 1179.62, 1217.66, 1235.65, 1280.59, 1313.71, 1428.78, 1475.76, 1895.74, 2194.12, 2752.45 |
| K3 | | |
| K4 | Hsp-60 | 833.39, 855.46, 912.59, 961.50, 1045.57, 1344.72, 1389.70, 1504.78, 1556.90, 1615.79, 1698.92, 1918.82, 2038.01, 2051.99, 2129.10, 2211.07, 2295.19, 2365.32, 2560.23, 3097.49, 3113.47 |
| K5 | Stathmin | 782.43, 817.42, 856.52, 870.55, 889.43, 912.47, 945.48, 959.54, 1025.53, 1039.49, 1045.54, 1067.48, 1074.57, 1088.56, 1153.64, 1165.55, 1179.56, 1260.60, 1326.69, 1388.75, 1406.66, 1499.78, 1541.84, 1624.79, 1740.70, 1756.73, 1878.83, 3323.81 |
| K6 | Rho GDI 2 | 731.44, 740.33, 855.49, 966.49, 974.39, 1084.61, 1185.63, 1311.69, 1475.81, 1692.78, 1708.71, 1939.56, 1953.66, 2611.16, 2944.22, 3005.51 |
| T1 | Thioredoxin peroxidase 2 | 819.43, 888.44, 894.44, 920.51, 980.53, 1107.60, 1164.56, 1196.64, 1211.68, 1359.81, 1622.85, 1750.96, 1778.97, 1794.95, 2085.99, 2420.18, 2781.30, 3597.66 |
| T2 | 60S ribosomal protein P0 | 720.42, 748.62, 771.42, 803.47, 968.58, 1109.46, 1217.69, 1221.64, 1234.63, 1280.64, 1313.73, 1428.84, 1638.87, 1707.79, 1896.02, 2194.09, 2262.92, 2398.98, 2501.19, 2584.16, 2752.36, 2872.32, 3178.64 |
| T3 | RNA binding regulatory subunit | 727.49, 755.48, 866.49, 883.53, 1158.61, 1287.77, 1337.75, 1671.90, 1673.91, 1675.76, 1691.77, 1707.74, 1831.74, 1847.68, 2041.09, 2584.28 |
| T4 | hnRNP C1/C2 | 731.30, 887.39, 903.36, 943.56, 1316.74, 1329.67, 1415.57, 1475.75, 1682.91, 1698.80, 1994.11, 2101.90, 2117.87 |
| T5 | hnRNP C1/C2 | 616.17, 756.47, 797.31, 887.41, 903.42, 943.58, 965.52, 981.44, 1235.54, 1316.79, 1329.67, 1682.95, 1707.76, 1790.84, 1851.80, 2294.19, 2383.94, 2717.03 |
| T6 | Proteasome subunit beta type 1 | 1007.58, 1009.48, 1033.48, 1146.61, 1347.80, 1531.86, 1545.76, 1651.85, 1667.81, 1893.92, 1998.05, 2003.99, 2338.25 |
| T7 | Pre-mRNA cleavage factor Im | 745.44, 810.43, 817.42, 831.40, 850.43, 932.53, 948.51, 1117.64, 1245.75, 1300.79, 1337.81, 1411.67, 1427.48, 1464.50, 1489.85, 1745.89, 1908.70, 2321.24, 2505.27 |
| T8 | Proteasome subunit alpha type 7 | 797.35, 825.39, 945.53, 1179.61, 1235.54, 1475.80, 1634.87, 1666.78, 1740.80, 1791.70, 2065.17, 2383.97, 2449.21 |
| T9 | U2 small nuclear ribonucleo-protein A' | 749.41, 798.61, 916.47, 930.40, 943.53, 1058.63, 1065.62, 1125.65, 1184.70, 1214.72, 1345.67, 1366.97, 1377.82, 1410.78, 1432.78, 1458.76, 1473.86, 1560.81, 1890.80, 2118.15, 2566.26, 2805.32, 3153.38 |
| T10 | GAP SH3 binding protein | 837.48, 1113.55, 1200.53, 1210.61, 1232.69, 1248.46, 1325.77, 1480.66, 1538.82, 1574.70, 1624.62, 1862.62, 1878.78, 1884.73, 1937.81, 2247.23, 2263.22, 2365.09, 2494.17, 2609.30, 2979.34, 3216.31 |
| T11 | DNA replication licensing factor MCM4 | 856.50, 1002.51, 1021.65, 1042.84, 1129.63, 1153.59, 1196.61, 1591.87, 1631.01, 1700.75, 1707.73, 1812.81, 1825.73, 1924.91, 1954.02, 2029.05, 2053.01, 2157.16, 2210.98, 2309.17; 2820.30 |
| T12 | Thioredoxin peroxidase 1 | 765.34, 789.41, 924.44, 972.55, 1023.58, 1033.49, 1045.49, 1065.44, 1179.64, 1211.69, 1334.72, 1734.93, 1851.80, 1862.90, 1928.64, 2019.15, 2084.94 |

TABLE 3a

| Name | Protein | Top Spot | Swiss-Prot | NCBI | Mw | Mw found | pI | pI found | Masses match | Sequence Coverage | Motif | $H_2O_2$ |
|---|---|---|---|---|---|---|---|---|---|---|---|---|
| BK1 | 40S ribosomal protein S21 | | P35265 | 464710 | 9.09 | 11.30 | 9.2 | 8.5 | 9 | 63% | Ribosomal | yes |
| BK2 | 40S ribosomal protein S12 | | P25398 | 133742 | 14.51 | 14.50 | 6.3 | 6.3 | 7 | 33% | Ribosomal | yes |
| BK3 | see K1 | | | | | | | | | | | yes |
| BK4 | Phosphoglycerate mutase 1 | 4_138 | P18669 | 130348 | 28.79 | 29.70 | 6.7 | 6.9 | 14 | 58% | PGAM | yes |
| BK5 | HCC-1 protein | | | 13940310 | 23.65 | 34.90 | 6.1 | 6.3 | 12 | 54% | SAP | yes |
| BK6 | see K2 | | | | | | | | | | | yes |
| BK7 | HnRNP A2/B1 | 4_285 | | 4504447/1 4043072 | 35.99/ 37.41 | 35.70 | 8.7/ 9.0 | 8.2 | 17 | 50%/48% | RNP | yes |
| BK8 | IMP dehydrogenase 2 | 2_708 | P12268 | 124419 | 55.79 | 54.10 | 6.4 | 6.7 | 25 | 52% | IMPDH, CBS | yes |

TABLE 3a-continued

| Name | Protein | Top Spot | Swiss-Prot | NCBI | Mw | Mw found | pI | pI found | Masses match | Sequence Coverage | Motif | H$_2$O$_2$ |
|---|---|---|---|---|---|---|---|---|---|---|---|---|
| BK9 | IMP dehydrogenase 2 | | P12268 | 124419 | 55.79 | 54.10 | 6.4 | 6.5 | 16 | 33 % | IMPDH, CBS | yes |
| BT1 | see T1 | | | | | | | | | | | yes |
| BT2 | see T4 | | | | | | | | | | | yes |
| BT3 | see T5 | | | | | | | | | | | yes |
| BT4 | see T10 | | | | | | | | | | | yes |
| BT5 | see T10 | | | | | | | | | | | yes |
| BT6 | hnRNP A/B | | | 14724990 | 35.95 | 39.10 | 6.5 | 6.6 | 16 | 33% | RNP | yes |

TABLE 3b

| Name | Protein | Masses of Fragments (Da) |
|---|---|---|
| BK1 | 40S ribosomal protein S21 | 723.33, 740.36, 950.48, 1038.56, 1053.55, 1054.53, 1122.53, 1136.54, 1138.51, 1152.52, 1194.67, 1262.68, 1278.67, 1503.91, 1556.75, 1570.81, 1586.76, 1795.86, 1809.86, 1811.80, 1825.81, 1840.86, 1923.91, 1939.90, 1970.01, 1983.98 1999.95 |
| BK2 | 40S ribosomal protein S12 | 970.57, 1042.55, 1056.58, 1066.65, 1075.60, 1089.62, 1134.64, 1203.71, 1262.77, 1284.75, 1475.86, 1585.90, 1726.04, 1765.13, 1779.11, 1794.17, 2163.08, 2193.00, 2257.11, 2271.18, 2287.24 |
| BK3 | see K1 | |
| BK4 | Phosphoglycerate mulase 1 | 757.52, 768.38, 975.50, 976.51, 1059.60, 1119.64, 1150.72, 1235.68, 1312.69, 1326.71, 1393.84, 1571.94, 1630.97, 1684.00, 1698.09, 1707.90, 1793.87, 1852.02, 1950.07, 1966.07, 1980.02, 1994.10, 2131.18, 2433.45, 2439.41, 2453.35 |
| BK5 | HCC-1 protein | 897.48, 935.55, 957.53, 960.57, 1069.63, 1079.65, 1101.61, 1105.62, 1119.68, 1133.68, 1173.66, 1187.69, 1201.61, 1207.75, 1247.79, 1260.61, 1286.78, 1302.78, 1310.82, 1324.83, 1344.83, 1358.85, 1360.87, 1434.85, 1475.90, 1489.84, 1499.93, 1513.98, 1586.03, 1603.79, 1642.04, 1760.15, 1775.06, 1872.01, 1886.07, 2060.16, 2156.08 |
| BK6 | see K2 | |
| BK7 | HnRNP A2/B1 | 733.44, 781.36, 861.54, 964.51, 995.47, 1013.48, 1087.53, 1101.54, 1188.71, 1202.71, 1256.60, 1270.62, 1327.68, 1359.69, 1377.72, 1410.76, 1475.86, 1589.96, 1639.00, 1677.85, 1695.90, 1709.91, 1799.08, 1813.02, 1826.99, 1838.11, 1852.02, 1880.11, 1894.09, 1927.11, 1941.15, 2143.86, 2189.77, 2205.81, 2219.76, 2233.87, 2277.22, 2386.27, 2496.21, 2843.66, 2859.48 |
| BK8 | IMP dehydrogenase 2 | 703.38, 724.34, 750.39, 844.53, 873.41, 954.53, 963.54, 972.54, 977.57, 986.57, 1063.58, 1100.61, 1156.70, 1307.83, 1325.84, 1444.82, 1481.98, 1495.98, 1671.97, 1693.02, 1707.03, 1780.13, 1821.14, 1892.19, 1965.26, 1979.21, 2048.28, 2086.22, 2131.1, 2555.34, 2569.52, 2881.67, 2897.66, 3263.84, 3278.85 |
| BK9 | IMP dehydrogenase 2 | 703.39, 724.35, 745.40, 794.46, 807.40, 881.45, 897.45, 946.50, 961.54, 972.53, 1033.54, 1063.60, 1100.61, 1156.70, 1234.72, 1277.92, 1307.74, 1325.69, 1349.85, 1444.82, 1482.02, 1639.00, 1692.98, 1780.12, 1821.12, 1892.20, 1915.10, 1965.28, 1994.17, 2048.26, 2086.29, 2131.20, 2309.33 |
| BT1 | see T1 | |
| BT2 | see T4 | |
| BT3 | see T5 | |
| BT4 | see T10 | |
| BT5 | see T10 | |
| BT6 | hnRNP A/B | 807.39, 862.45, 928.56, 958.57, 990.58, 1024.59, 1029.57, 1065.60, 1089.55, 1114.71, 1171.73, 1181.65, 1302.80, 1343.73, 1361.78, 1393.86, 1455.85, 1471.83, 1499.82, 1517.89, 1629.01, 1707.94, 1773.15, 1798.14, 1841.08, 1855.03, 1872.13, 1954.23, 1969.12, 2061.03, 2499.45 |

TABLE 4

| | | % PI positive cells | | |
|---|---|---|---|---|
| Incubation with DPI | Addition of AEX-21 | mean(n = 3) | standard deviation | control subtracted |
| − | − | 6.7% | 0.7% | |
| − | + | 67.0% | 3.1% | 60.3% |
| + | − | 8.0% | 0.7% | |
| + | + | 40.7% | 4.4% | 32.7% |

The invention claimed is:

1. An isolated polypeptide obtainable from *Aplysia*, comprising at least one of the amino acid sequences selected from the group consisting of:

(SEQ ID NO. 2)
(Asp/Gln)-Gly-(Ile/Val)-Cys-Arg-Asn-(Gln/Arg)-Arg-(Gln/Pro), and (SEQ ID NO.7)
Asp-Ser-Gly-Leu-Asp-Ile-Ala-Val-Glu-Tyr-Ser-Asp-Arg wherein the polypeptide has cytotoxic activity which is resistant against proteolytic digestion.

2. The polypeptide of claim 1, which has a molecular mass of about 60±5 kDa as determined by SDS-PAGE.

3. The polypeptide of claim 1, which has cytotoxic activity towards the human T cell line Jurkat.

4. The polypeptide of claim 1, which is resistant against proteolytic digestion and maintains cytotoxic activity when incubated with N-acetyl neuraminic acid.

5. A pharmaceutical composition, comprising as an active agent a polypeptide of claim 1, and a pharmaceutically acceptable carrier.

6. A method for treating a disease associated with apoptosis resistant cells by administering a polypeptide of claim 1 to a subject having said disease.

7. The method of claim 6, wherein the disease is a tumor.

8. A method for treating a tumor by administering an anti-tumor effective amount of a pharmaceutical composition of claim 5 to a subject having said tumor.

9. A method for producing a fragment of a polypeptide obtainable from *Aplysia* having cytotoxic activity comprising: subjecting said polypeptide to proteolytic digestion, wherein said fragment has cytotoxic activity and comprises at least one amino acid sequence selected from:

(SEQ ID NO.2)
(Asp/Gln)-Gly-(Ile/Val)-Cys-Arg-Asn-(Gln/Arg)-Arg-(Gln/Pro), and (SEQ ID NO.7)
Asp-Ser-Gly-Leu-Asp-Ile-Ala-Val-Glu-Tyr-Ser-Asp-Arg

10. The method according to claim 9, wherein said proteolytic digestion is performed by pronase, trypsin or proteinase K.

* * * * *